United States Patent [19]

Yano et al.

[11] Patent Number: 5,298,614
[45] Date of Patent: Mar. 29, 1994

[54] SIZE LIMITED DOUBLE STRANDED POLY I POLY(CYTIDYLATE/4-THIOURIDYLATE)

[75] Inventors: Junichi Yano, Nara; Tadaaki Ohgi, Otsu, both of Japan

[73] Assignee: Nippon Shinyaku Co. Ltd., Japan

[21] Appl. No.: 319,062

[22] Filed: Apr. 6, 1989

Related U.S. Application Data

[63] Continuation-in-part of Ser. No. 212,899, Jun. 29, 1988, abandoned, which is a continuation-in-part of Ser. No. 174,985, Mar. 29, 1988, abandoned, which is a continuation-in-part of Ser. No. 672, Jan. 6, 1987, abandoned.

[30] Foreign Application Priority Data

Jan. 6, 1986 [JP] Japan .................................. 61-1076
Jul. 3, 1987 [JP] Japan .............................. 62-167433
Jul. 3, 1987 [JP] Japan .............................. 62-167434

[51] Int. Cl.$^5$ ............................................ C07H 21/02
[52] U.S. Cl. .................................. 536/25.5; 536/23.1; 536/25.1; 536/28.53
[58] Field of Search ................................. 536/27–29; 514/44

[56] References Cited

U.S. PATENT DOCUMENTS 4,315,919  2/1982  Shanbrom ............................ 530/384

FOREIGN PATENT DOCUMENTS 2038628  7/1980  United Kingdom .................. 514/44

OTHER PUBLICATIONS

Kochetkov et al., Organic Chemistry of Nucleic Acids, Part A, Plenum Press, New York, N.Y., 1971, see pp. 20 and 238.
Lehninger, Biochemistry, 2nd Ed., Worth Publishers, New York, N.Y., 1975, see pp. 159–160 and 966–972.
Thompson et al., Methods in Enzymology, vol. 100, 369–399 (1983).
Wells et al., Methods in Enzymology, vol. 65, 327–347 (1980).
Kanter et al., Anal. Biochem. 97, 77–84 (1979).
Ho et al., "Enzymatic Synthesis of Polyuridylic Acid Containing Modified Bases," *Nucleic Acids Res.*, 8(14), 3175–3191 (1980).
Favre et al., "Intramolecular Cross-linking of Single-Stranded Copolymers of 4-Thiouridine and Cytidine," *Biochem. Biophys. Res. Comm.*, 58(2), 507–515 (1974).
Iris L. Doerr, I. Wempen, Donald A. Clarke and Jack J. Fox, *Journal of Organic Chemistry*, vol. 26, pp. 3401–3409 (1961).

*Primary Examiner*—Johnnie R. Brown
*Assistant Examiner*—L. Eric Crane
*Attorney, Agent, or Firm*—Rosenman & Colin

[57] ABSTRACT

Nucleic acid derivatives and pharmaceutical compositions containing such derivatives are produced containing one 4-thiouridylic acid for every 6 to 39 cytidylic acids present, which has a length of from 50 to 10,000 base pairs. Methods of treatment using these nucleic acid derivatives to treat viral infections is also described.

3 Claims, 7 Drawing Sheets

SIZE LIMITED DOUBLE STRANDED POLY I POLY(CYTIDYLATE/4-THIOURIDYLATE)

This is a continuation-in-part of our copending application Ser. No. 07/212,899 filed Jun. 29, 1988, now abandoned, which is a continuation-in-part of our copending application Ser. No. 07/174,985 filed Mar. 29, 1988, now abandoned, which is a continuation-in-part of our copending application Ser. No. 07/000,672 filed Jan. 6, 1987, now abandoned.

The present invention relates to nucleic acid derivatives useful as pharmaceuticals and to a process for the production thereof.

It is known in the art that nucleic acid is composed of sugars such as ribose bonded to purine or pyrimidine, and that they are arranged in chains via phosphoric acid. Among nucleic acids, RNA (ribonucleic acid polymer) is a high molecular compound in chain structure in which ribose is contained as a sugar and sugar moieties are combined through diester bonds of phosphoric acid.

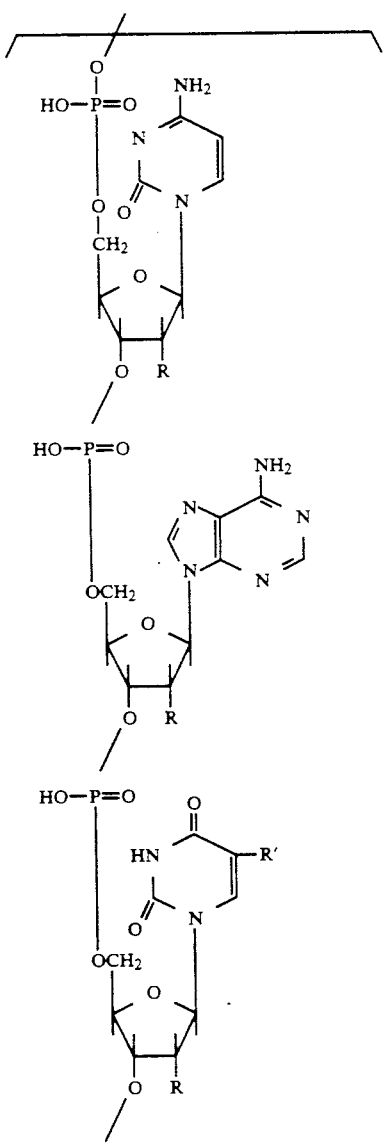

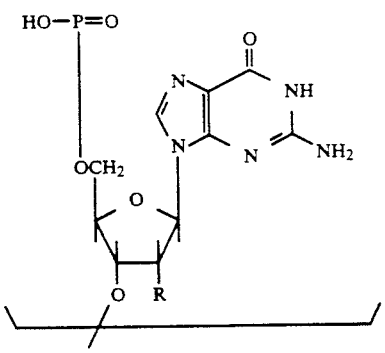

Ribonucleic acid (R = OH, R' = H);
Deoxyribonucleic acid (R = H, R' = CH₃).

The double stranded is in helical spiral form and its steric structure by a complementary base pair combination by hydrogen bond of purine or pyrimidine ring moieties of the base (e.g. inosine, cytidine, uridine, etc.) which constitutes nucleic acid. Nucleic acids having double strands exhibit useful physiological activity and, accordingly, many studies have been done on them.

Among them, natural RNA derived from virus and synthetic double stranded RNA such as polyinosinic acid-polycitydylic acid derivatives (hereinafter abbreviated as "poly I:poly C"), polyadenylic acid-polyuridylic acid derivatives, etc. have been studied by many:

Field et al: Proc. Nat. Acad. Sci. U.S. 58, 1004, (1967);
Field et al: Proc. Nat. Acad. Sci. U.S. 58, 2102, (1967);
Field et al: Proc. Nat. Acad. Sci. U.S. 61, 340, (1968);
Tytell et al: Proc. Nat. Acad. Sci. U.S. 58, 1719, (1967);
Field et al: J. Gen. Physiol. 56, 905 (1970);
De Clercq et al: Methods in Enzymology, 78, 291 (1981).

These references are summarized as follows.

A List of Synthetic Nucleic Acid Derivatives as Interferon Inducers.
(I) Homopolymer-homopolymer Complexes (Double Strand Nucleic Acid Polymer in which Poly I:Poly C is a Mother Structure):
(1) Base Modifications
Polyinosinic acid-poly(5-bromocytidylic acid);
Polyinosinic acid-poly(2-thiocytidylic acid);
Poly(7-deazainosinic acid)-polycytidylic acid;
Poly(7-deazainosinic acid)-poly(5-bromocytidylic acid);
Polyinosinic acid-poly(5-thiouridylic acid)
(2) Sugar Modifications
Poly(2'-azidoinosinic acid)-polycytidylic acid
(3) Phosphoric Acid Modifications
Polyinosinic acid-poly(cytidyl-5'-thiophosphoric acid)
(II) Interchanged Copolymers:
Poly(adenylic acid-uridylic acid)
(III) Homopolymer-Copolymer Complexes:
Polyinosinic acid-poly(cytidylic acid-uridylic acid);
Polyinosinic acid-poly(citydylic acid-4-thiouridylic acid).
(IV) Complexes of Synthetic Nucleic Acid with Polycation:
Polyinosinic acid-polycytidylic acid-poly-L-lysinecarboxy-methylcellulose complex (called "Poly ICLC").
(V) Others:
Polyinosinic acid-poly(1-vinylcytosine).

As illustrated hereinabove, there have been many reports on double stranded RNAs, especially derivatives of poly I:poly C, in recent years. There is also a review on a series of nucleic acid derivatives including the above as well as their relations between the chemical structure and activity (e.g. De Clercq, et al):

Texas Reports on Biology and Medicine, 41, 77 (1982).

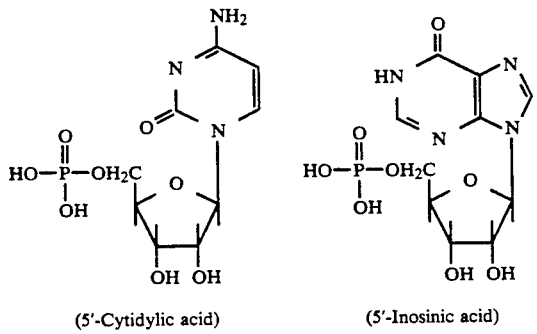

(5'-Cytidylic acid)  (5'-Inosinic acid)

In those references, there is a particular description that nucleic acid polymers are to be with high molecules of 4S or more when they exhibit interferon-producing activity.

As such, many RNA nucleic acid derivatives, not only single stranded but also double stranded or even polystranded ones which are complementary have been synthesized and their physiological activities have been studied.

The poly I:poly C is a substance having a significant activity. Its usefulness has been evaluated and studies have been conducted thereon.

The physiological activities such as interferon inducing action, proliferation inhibiting action for tumor cells in cancer-bearing mammalians (cf. Levy: Proc. Nat. Acad. Sci. U.S., 62, 357 (1969) and an immune system activating action in vivo (cf. Carter: J. Immunol. 104, 1035 (1970) have been known.

As mentioned above, clinical applications of antiviral and anti-cancer activities of poly I:poly C have been expected. Unfortunately, in the meanwhile, it has been found that it exhibits unexpectedly strong toxicity and there is a problem in its administration to humans. Still there have been many attempts to utilize poly I:poly C derivatives for therapy. For example, Levy et al have developed poly ICLC exhibiting strong interferon-inducing activity (cf. Levy et al: Texas Reports on Biology and Medicine, 41, 653, 1982)).

Among the derivatives of poly I:poly C, those modified with bases will be exemplified below.

Studies for polycytidylic acid have also been conducted and there is a report (British Patent Application No. 2,038,628) stating that, when a mercapto group (—SH) is introduced to an extent of 50% or more in place of —NH$_2$ groups of the pyrimidine ring of polycytidylic acid, the physiological activity increases.

One example which is known is that double stranded RNA consists of poly I and poly C bearing 4-thiouridine as a copolymer (A. Favre, et al: Biochemical and Biophysical Research Communications, 58, 507 (1974) and others). Its physiological activities have not been mentioned at all in the above article though.

These kinds of double stranded RNAs which are not complementary, have been known as, so-called "mismatched" or "loop-out" structures which, exist in the naturally occurring RNAs such as transfer tRNAs, ribosomal RNAs and the viral RNA secondary structures.

A compound in which only a few parts of cytidine in the poly I:poly C is changed to uridine (i.e. mismatched RNA) has been studied because of its physiological activity similar to that of poly I:poly C (cf. Japanese Laid Open 50/082226).

This patent describes the idea of the combination of a mismatched RNA with an interferon inducer. Incidentally, poly I:poly C had already been knwon as an inducer before the above patent was laid open.

The above compound is known to have low toxicity but such an effect was achieved not only by a mismatching but also by some other factors resulting from its chemical structure.

However, there has been no study in which the relationship between the chain length and physiological properties is discussed.

The conventional physiologically active substances described above can be expected to exhibit useful effects though they exhibit toxicity as seen in the poly I:poly C(De Clercq et al: Infect. Immuni., 6, 344, 1972). It would therefore be desirable if the toxicity could be reduced and the activity increased.

We have found that RNA can form stabilized derivatives of high conformation by certain covalent bonding. When the physiological activity was measured, it has been found that they exhibit far stronger activity as compared with the conventional physiologically active substances with very low toxicity.

In addition to the above-given finding (which will be called "the first feature of the present invention"), it has been further found, when the chain length of the double stranded nucleic acid derivatives is limited to certain ranges, the resulting substances exhibit desired physiological activity with markedly less toxicity. This finding will be called "the second feature of the present invention."

The gist of the second feature of the present invention is that, regardless of the introduction of sulfur atoms thereinto, the chain length of the double stranded nucleic acid polymer is limited to a certain range.

More particularly the present invention is a nucleic acid derivative wherein the purine or pyrimidine ring in the nucleic acid polymer is substituted with at least one SH group, or said derivative contains a disulphide bond, or both.

According to one embodiment of the present invention the nucleic acid polymer of nucleic acid derivative is a single stranded ribonucleotide polymer.

According to a further embodiment of the nucleic acid derivatives of the present invention, the single stranded ribonucleotide polymer is a poly C containing certain proportions as specified below of 4-thiouridylic acid containing sulphur atoms as a result of substituting an —NH$_2$ group in a pyrimidine ring of the cytidylic acid in the poly C with an —SH group. The polymer length is preferably 50 to 10,000 as calculated by base pair numbers.

According to a further embodiment of the present invention, the number of sulphur atoms, in the nucleic acid derivatives, to 6 to 39 of cytidylic acid present in the poly C, is one.

According to a further embodiment of the present invention the nucleic acid polymer is a double stranded ribonucleotide polymer.

According to a further embodiment of the present invention the double stranded ribonucleotide polymer is composed of poly I and poly C containing certain proportions as specified below of 4-thiouridylic acid containing sulphur atoms by substituting the —NH$_2$ group in the pyrimidine ring of cytidylic acid in the poly C with an —SH group. The polymer length is preferably 50 to 10,000 calculated as base pair numbers and the number of sulphur atoms, in the nucleic acid derivatives, to 6 to 39 of cytidylic acid present in the poly C, is preferably one.

Some of the nucleic acid derivatives of the present invention can be synthesized from nucleic acid base to which —SH groups can be introduced. Specific examples of the present invention nucleic acid derivatives are those having a complementary double spiral structure of a chain compound (called "poly C" in this specification) which is a cytidylic acid polymer and another chain compound (called "poly I" in this specification) which is an inosinic acid polymer. Though said compound exhibits the structure similar to the already known poly I:poly C, the nucleic acid derivatives of the present invention have better i.e. more potent, activity and lower toxicity.

The nucleic acid derivatives of the present invention form derivatives by a partial substitution by sulphur (SH), by covalent linkage (S—S bond), or by both.

The sulphur atoms in the nucleic acid derivatives of the present invention can be introduced, before or after the polymer preparation, by utilizing a chemical synthesis or an enzymatic reaction. The introduction is conducted by substituting nucleic acid base with —SH groups such that an —NH$_2$ group in a pyrimidine ring of cytidylic acid is substituted with an —SH group. The substituent residue is called 5'-4-thiouridylic acid.

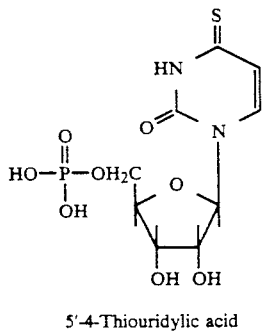

5'-4-Thiouridylic acid

The introduced —SH group is further oxidized by a suitable method as described below so that the S—S bond bridge can be formed.

Derivatives having both —SH and S—S groups in a molecule can be prepared either by a partial oxidation of a compound in which —SH is introduced or by a partial reduction of a compound in which S—S is introduced.

The nucleic acid polymer (poly C) is single stranded. The single stranded nucleic acid polymer after formation of the —SH substitution or the S—S bond bridge can be associated with a complementary single stranded nucleic acid polymer, by a suitable method as described below, to form multiple strands. Conversely, it is also possible that the firstly-sulphurized single stranded nucleic acid polymer is associated with the complementary nucleic acid polymer to form multiple strands followed by oxidation to give an S—S bond bridge. The nucleic acid derivatives thus prepared are also included as part of the present invention. Thus, all nucleic acid polymers are included in the present invention so far as they contain nucleic acid bases to which an —SH group has been introduced. For example, the compounds obtained by disulphidation of nucleic acid polymers containing 4-thiouridine,2-thiouridine,2-thioguanosine,6-mercaptopurine, 8-mercaptopurine, etc. are included in the present invention.

The nucleic acid derivatives of the present invention can be cleaved at their phosphoric acid side chain to give lower molecular compounds and such lower molecular ones are also included in the present invention. Accordingly, in this sense, there is a difference between the present invention and the conventional poly I:poly C.

Examples of the nucleic acid derivatives of the second feature of the present invention are those which are prepared by shortening of the chain of the substances mentioned in the List of Synthetic Nucleic Acid Derivatives to the restricted molecular size. The resulting substances still exhibit the fundamental structures which are the same as that of the poly I:poly C but the characteristic point of the nucleic acid derivatives of the present invention is that their molecular size is restricted to a specific range.

Examples of the nucleic acid derivatives of the present invention falling into the category of the second feature are as follows:

Polyinosinic acid:poly(5-bromocytidylic acid) wherein S value is 4 to 13 and, preferably, molecules of the maximum distribution are 100 to 600 calculated as number of bases;

Polyinosinic acid:poly(2-thiocytidylic acid) wherein S value is 4 to 13 and, preferably, molecules of the maximum distribution are 100 to 600 calculated as numbers of bases;

Poly(7-deazainosinic acid):polycytidylic acid wherein S value is 4 to 13 and, preferably, molecules of the maximum distribution are 100 to 600 calculated as numbers of bases;

Poly(7-deazainosinic acid):poly(5-bromocytidylic acid) wherein S value is 4 to 13 and, preferably, molecules of the maximum distribution are 100 to 600 calculated as numbers of bases;

Poly(2'-azidoinosonic acid):polycytidylic acid wherein S value is 4 to 13 and, preferably, molecules of the maximum distribution are 100 to 600 calculated as numbers of bases;

Polyinosilic acid:poly(cytidyl-5'-thiophosphoric acid) wherein S value is 4 to 13 and, preferably, molecules of the maximum distribution are 100 to 600 calculated as numbers of bases;

Poly(adenylic acid-uridylic acid) wherein S value is 4 to 13 and, preferably, molecules of the maximum distribution are 100 to 600 calculated as numbers of bases;

Polyinosinic acid:poly(cytidylic acid, uridylic acid) wherein S value is 4 to 13 and, preferably, molecules of the maximum distribution are 100 to 600 calculated as numbers of bases;

Polyinosinic acid:poly(cytidylic acid, 4-thiouridic acid) wherein S value is 4 to 13 and, preferably, molecules of the maximum distribution are 100 to 600 calculated as numbers of bases;

Polyinosinic acid:polycytidylic acid:poly-L-lysine wherein S value is 4 to 13 and, preferably, molecules of the maximum distribution are 100 to 600 calculated as numbers of bases; and Polyinosinic acid:poly(1-vinylcytosine) wherein S value is 4 to 13 and, preferably, molecules of the maximum distribution are 100 to 600 calculated as numbers of bases.

Polyinosinic acid:poly(1-vinylcytosine) wherein S value is 4 to 13 and, preferably, molecules of the maximum distribution are 100 to 600 calculated as numbers of bases.

In the manufacture of the nucleic acid derivatives of the present invention, the phosphoric acid moiety on the side chain of the polymer derivatives mentioned in the already-given list or the above-given polymers is cleaved so that their molecular weight can be lowered.

Examples of the applicable methods for such low molecularization are that, besides the thermal decomposition which will be illustrated later, partial hydrolytic method utilizing RNAases, alkali limitive hydrolysis of RNA restricted enzymatic reaction utilizing PNPases, etc.

As a result of the characteristics of the second feature of the present invention that the control or limitation of the molecular size distribution by a low molecularization due to cleavage of the phosphoric acid moiety on side chain, the effects of the present invention, i.e. firstly that physiological activity can be highly maintained and secondly that the safety can be increased, can be achieved for the first time.

Nucleic acid derivatives of the second feature of the present invention also cover, besides the above-given poly I:poly C, a series of compounds wherein a part of the cytidylic acid in the poly I:poly C is substituted with 5'-uridylic acid or 5'-4-thiouridylic acid.

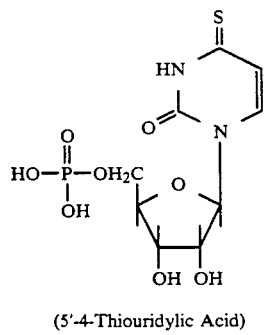

(5'-4-Thiouridylic Acid)

The present invention also includes applications to modified bases such as 5'-5-thiouridylic acid, 5'-6- thiouridylic acid and 5'-2-thiouridylic acid.

As a result of the characteristic feature of the nucleic acid derivatives of the present invention, i.e. substitution with —SH, formation of cross linking by S—S bond or both, and formation of low molecular substances by a cleavage of the phosphoric acid side chain, it is possible for the first time to obtain the benefits of the present invention that (1) enough physiological activity is preserved and (2) safety is increased because of lower toxicity.

The nucleic acid derivatives of the present invention are useful for their strong action as interferon inducers.

In addition they are useful for their TNF-productive ability, interleukin 1 productive ability, interleukin 2 productive ability, macrophage activating ability, activating ability on NK cell, inhibiting action for proliferation of tumor cells, inhibition action for proliferation of tumors in cancer-bearing mice, inhibition action for proliferation in nude mice bearing cancer of human tumor cells.

Nucleic acid derivatives of the present invention have lower toxicity and hence are far more safe as compared with interferon inducers such as conventional poly I:poly C. Accordingly, the compounds of the present invention are useful as antiviral agents and antitumor agents.

The present inventors found, on the basis of the abovementioned prior art, that when poly-I.poly-C and various derivatives thereof having poly-I.poly-C moiety as the parent body are sized so that the whole molecular size distribution of the derivatives may fall within the range of from 4S to 13S as the sedimentation constant value thereof (or from about 50 to 10000 or so as the number of bases of the derivatives), the thus sized derivatives may have a noticeably lowered toxicity and may still have the physiological activities which will be mentioned below. Accordingly, the present inventors filed patent applications in the Japanese Patent Office (Japanese Patent Application No. 62-167433 and another Patent Application with the priority of said Application No. 62-167433).

Along with the above-mentioned study, the present inventors further investigated various means of efficiently obtaining the above-mentioned products. Specifically, they have investigated various means of sizing nucleic acid derivatives to have a molecular size distribution of from 50 to 10,000 or so as the number of bases thereof and a means of forming a double-stranded nucleic acid polymer from two kinds of single-stranded nucleic acid polymers. Regarding the former means, the operation of restricting the molecular size distribution of nucleic acid derivatives to a determined range is called "sizing" herein. Since the sizing is accompanied by conversion into low molecular substances in accordance with the method of the present invention, the sizing includes "chain-shortening". Regarding the latter means, this is called "annealing" hereinafter.

The term "base pair" (abbreviated as "bp") frequently used to indicate the molecular size of nucleic acid is used to indicate the molecular size by the numbers of bases in the nucleic acid (i.e. 10 bp means the double strand polymer having ten bases) in each complementary strand. Since nucleic acid polymers other than double stranded polymers are also referred to in the present specification, the term "residue numbers" in place of bp will be used. Thus "10 residue numbers" means the nucleic acid polymer having 10 bases in a strand.

In specifying the molecular size of nucleic acid, conventional sedimentation constant (i.e. S value) has been widely used. However, the present inventors have succeeded in calculating the above-given base numbers by utilizing an electrophoretic method or a high performance liquid chromatographic method (HPLC) using a gel filtration column (which will be illustrated later) followed by comparison with the control which is a double stranded DNA (M 13 phage fragment) with known base pairs.

Hitherto, a sedimentation constant value (S value) has widely been utilized for representation of the molecular weight of macromolecular nucleic acid substances. Macromolecular nucleic acid substances which are commercially available are represented by means of the S value thereof. However, because of the progress of experimental techniques in recent years, a means of more accurately determining the molecular weight of macromolecular substances has been established by the use of gel electrophoresis, gel filtraton chromatography, ion-exchange chromatography or the like so that the determination of the chain length of macromolecular nucleic acid substances has become possible. Therefore, the relation between the representation by S value and the representation by chain length becomes problematic. This is especially so, since the respective nucleic acid molecules have their intrinsic values in the case of the representation by S value, there is not always any problem on the point as to whether or not the representationby S value and the representation by chain length could accurately correspond with each other as a means of representing the molecular weight of nucleic acids.

Accordingly, for the presentation of the molecular weight of the nucleic acid polymers of the present invention, the representation by S value is also employed in the description of the present invention in accordance with conventional usage in the field of nucleic acid chemistry. However, since the "S value" is one obtained by a method of measuring the molecular weight of macromolecular nucleic acid substances in the form of a molecular mass as a whole (or in the form of a molecular state of the substance), the representation on the basis of the measurement of the chain length of the substance (which is "base number") as herein referred to) is also mentioned herein along with the "S value". This is especially because the boundary in the molecular weight distribution is required to be more definitely represented in the embodiment of the present invention.

In accordance with conventional means of sizing poly-I:poly-C and various derivatives thereof having poly-I:poly-C as the parent body to give sized double-chain nucleic acid polymers, already existing double-stranded nucleic acid polymers are decomposed into low molecular compounds, that is, double-stranded nucleic acids are hydrolyzed into low molecular compounds after annealing single-stranded nucleic acid. However, the conventional means are inconvenient for obtaining the intended product on an industrial scale since the sizing requires a long time and the process could not be performed rapidly. In addition, the conventional means are not always satisfactory from the view point of the yield of the products.

On the other hand, if single-stranded nucleic acid polymers are, after sizing, required to be sulfurized, the polymers are sulfurized with hydrogen sulfide and then the hydrogen sulfide is evaporated out from the solvent, in accordance with a conventional method. Thus, pyridine is evaporated out from the reaction solution, after sufurization, for example, with a vacuum pump so that hydrogen sulfide may be removed out from the reaction solution together with pyridine by evaporation. By that method, however, hydrogen sulfide vaporizes in air, and therefore, the performance of that method in an industrial scale is disadvantageous from the viewpoint of environmental pollution. In addition, in accordance with that method, the aqueous layer separated after evaporation of pyridine is put into a dialyzing tube for dialysis against running water so as to obtain the intended product. However, the method requires at least 3 days for the complete operation and the yield of the product is at most 80% or so. Thus the conventional method has various technical problems from the point of the yield of the products, the manufacturing cost and the operational time.

The sizing technique itself could not be said to be free of difficulties either.

In this technical field, it is generally the case that a nucleic acid polymer is heated in the presence of formamide so as to hydrolyze it into low molecular compounds. In this conventional method, products with a desired chain length are obtained by properly controlling the reaction time and the reaction temperature, and then the reaction solution is subjected to dialysis so as to remove any excess decomposed compounds having an excessively lower molecular size. In accordance with the conventional method, however, compounds with various different molecular weight distributions would be formed by sizing, even though the reaction condition is kept constant, in accordance with the properties of the nucleic acid polymers used. Therefore, the method has a problem with lack of reproducibility. The reason is considered because, as the starting materials for use in the method are prepared by an enzyme reaction, the size of the starting materials could not be defined to be constant. In addition, by the dialysis as applied to the method it is in principle impossible to remove nucleic acid polymers having a longer chain length than the products formed. Under the circumstances, a fundamental means of overcoming the abovementioned problems in the prior art is desired.

Accordingly, the present inventors investigated various ways of attaining the following objectives:

(1) Sized double-stranded nucleic acid polymers are obtained as products by a rapid process.

(2) The yield of the products is high.

(3) Even when the process is performed on an industrial scale, the process does not cause environmental pollution and other related problems.

(4) A series of the operation for the process in sufficiently quantitative and reproducible.

Nucleic acid derivatives of the present invention contain substances with various molecular sizes and are generally preferred, not in terms of safety but at least in terms of activity, that the size is not less than 50 residue numbers e.g., 50 to 10,000 residue numbers. It is known in the art that the molecular size of even far larger than 10,000 residue numbers has only a slight influence in maintaining the physiological activities. According to the present invention the undesired toxic effects occur over the above residue numbers.

In the present invention, the base number is shown by the UV absorbance detection or the stain range with methylene blue of the nucleic acid residues in a native form condition on such as agarose gel electrophoresis or HPLC gel filtration.

If the double stranded RNA molecule having 5'-end labelling with $^{32}P$ was measured by beta-ray detection in a denatured form condition containing methyl mercurous hydroxide, the molecular number should be obtained in a different value from the above case.

For example, the number of 50 to 10,000 base residue in total molecules in a "native form" may correspond with the molecular number having about 30 to 1,500 base chain length in a molecule in a denatured form.

In giving numbers of sulphur in the nucleic acid derivatives of the present invention, the degree of sulphurization (n) is used in this specification. Cytidylic acid changes to 4-thiouridylic acid by substituting the —NH$_2$ group in the pyrimidine ring with the —SH and the "n" indicates the numbers of cytidylic acid existent to one 4-thiouridylic acid. The nucleic acid derivatives of the present invention contains substances with many kinds of "n" and it is preferred that said n is not less than 6. When n is less than that, it has been confirmed that the physiological activity decreases. When n is 6 or more, there will be no further limitation and it may be as many as 39 and there is a little influence of n on the physiological activity of the present invention.

The second feature of the present invention is further illustrated below.

The present inventors have conducted studies using both inhibition of cancer cells in cancer-bearing mice and lesion to bone marrow stem cells of mice as indexes at the same time have found that there are both activity and toxicity when the nucleic acid polymer has a molecular size distribution of more than 13S (by a sedimentation constant), that there is activity while toxicity is markedly reduced when the value is within a range of 4S to 13S, and that there is neither activity nor toxicity when the value is less than 4S.

The fact that activity disappears when the value for poly I:poly C is less than 4S nearly agrees with the result by De Clercq already referred to. However, there has been no report at all of a study of the relationship between the chain length and toxicity.

Thus, the fact that the control of the molecular size (i.e. chain length) of nucleic acid polymers within a specified range is the primarily important factor for remarkable reduction of toxicity of poly I:poly C and derivatives thereof was first discovered by the present inventors.

The preferred molecular size distribution requires control within a range of 4S to 13S by a sedimentation constant and of 50 to 10,000 by base numbers. In that case, the chain length in the maximum distribution is generally from 100 to 600 base numbers.

In manufacturing the nucleic acid derivatives of the present invention, various methods can be used. The poly C and the like which are starting materials of the present invention derivatives are readily available. The poly C may be easily sulphurized by, for example, the reaction with sulphurizing agent such as hydrogen sulphide. As a result of said reaction, certain numbers of cytidylic acid in the poly C can be changed to 4-thiouridylic acid. When the reaction conditions such as reaction temperature and reaction time are varied, poly C with desired "n" values can be prepared. The sulphurized poly C can be annealed with poly I in order to form a duplex complex in physiological condition, which is readily obtained by known methods. The sulphurized poly C:poly I obtained as such can be introduced to the nucleic acid derivatives of the present invention by a disulphide production reaction such as, for example, oxidation with an iodine reagent.

The nucleic acid derivatives of the present invention can be obtained almost quantitatively by the above methods and the overall yield is around 90%.

In the case of synthesis of other nucleic acids such as poly A:poly U having a disulphide bridge, the polymer is first prepared by an enzyme reaction using a nucleic acid base containing sulphur atom therein. Conventional methods in the manufacture of heteropolymers can be used.

Typical examples will be that, when 36 mM of uridine-5'-di-phosphate (UDP) and 7 mM of 4-thiouridine-5'-diphosphate (S⁴ UDP) are made to react at 37° C. for 5 hours in 150 mM of Tris buffer (pH 8.2) containing 10 mM magnesium chloride and 0.4 mM EDTA using 0.5 unit/ml of polynucleotide phosphorylase (PNPase, type 15, PL Biochemical), a heteropolymer in which one 4-thiouridine is contained for 13 uridine residue is obtained in around 50% yield. When 2-thiouridine-5'-diphosphate is used in place of 4-thiouridine-5'-diphosphate, a poly U containing 2-thiouridine is obtained.

Once a nucleic acid polymer containing —SH groups is prepared as such, the following derivatives can be obtained by the same operation as the case of sulphurized poly I:poly C described in the Examples. More specifically, both sulphurized polyuridylic acid and equimolar polyadenylic acid are dissolved in neutral aqueous solution and subjected to an annealing for a complex formation.

Thus, after dissolving in water in an incubator, the temperature is gradually raised to 85° C., then kept at 85° C. for 10 minutes, and allowed to stand at room temperature.

The complex thus obtained is oxidized with the same conditions as in the disulphidated complex of poly I:poly C to give poly A:poly U derivatives having a disulphide bridge. The yield after the annealing is about 80% and the overall yield is about 40%.

The disulphide complex is well dialyzed against a neutral aqueous solution and lyophilized to give white and fibrous solid.

The nucleic acid derivatives of the present invention give a certain clear melting curve as described later and, accordingly, it is apparent that they exhibit stable fundamental structures.

If the stabilization of the double stranded complex formation in nucleic acid polymer is shown with reference to the 50% melting temperature (Tm value), poly I:poly C has a 59.0° C. under a neutral condition in aqueous buffer solution containing 0.1M sodium ion while the SH-substituted nucleic acid derivative containing 4-thiouridine (n=20) and the S-substituted nucleic acid derivative (n=20) have a 59.5° C. and 59.3° C., respectively. In the case of OH-substituted nucleic acid derivative containing uridine at the rate of n=20 the same as above, the value is as low as 53.1° C.

Thus the introduction of sulphur atoms is more effective in stabilizing higher structure of the nucleic acid as compared with other substituted derivatives such as those substituted with $NH_2$ or with OH.

Then the resistance against hydrolysis by RNase was compared in terms of the time ratio until the hydrolysis arrives at 50%. Thus, under conditions such as venom phosphodiesterase enzymatic reaction, poly I:poly C was 50 minutes while those of nucleic acid derivatives containing 4-thiouridine (SH group) and its S—S bond (n=20) are 60 minutes and, by contrast, those of nucleic acid derivatives (n=20) containing uridine (OH group) were as short as 20 minutes. It is therefore apparent that sulphur atoms exhibit an effect on biochemical stability.

Further manufacturing steps are described below.

In the case of sizing of each single stranded nucleic acid polymer prior to annealing, the desired products in which the molecular distribution size is within a range of 4S to 13S (about 50 to 10,000 in terms of base numbers) can be promptly obtained by utilizing that fact that, in place of conventional electrophoresis, the use of gel filtration of high performance indication of the molecular distribution and thereby in easy confirmation of changes in distribution of molecular size. Further, after the sizing, the conventional dialysis step is replaced by a very simple step comprising the addition of a lower alcohol.

When sulphurization of the single stranded nucleic acid polymer is required after sizing, the conventional method of sulphurizing with hydrogen sulphide followed by direct evaporation of hydrogen sulphide from the reaction mixture is replaced by a very simple step comprising the addition of an aryl alcohol followed by centrifugal separation to increase the yield.

As a method of controlling and restricting the molecular weight distribution of the sized single-stranded nucleic acid polymers, an ion-exchange resin is employed. (This operation is herein referred to as "size-restriction".)

The present invention will be explained in detail hereinbelow.

Annealing is a step of binding complementary single-stranded nucleic acid polymers into a double-stranded polymer, and this is an operation which can naturally be performed with ease. If sizing is performed after annealing, the sulfurized degree would erroneously fluctuate so that it would become difficult to quantitatively obtain the product. Accordingly, the present inventors have tried to perform the sizing operation prior to the annealing step and, as a result, an extremely excellent result has been obtained. The abovementioned aspect (1) has a close relation to the aspect (2). In accordance with the conventional means of determining a molecular weight by electrophoresis, at least one full night is required for migration, staining and other steps, and therefore, rapid procedure is difficult. According to the present invention, as opposed to this, HPLC gel-filtration is applied to the determination of the molecular weight of nucleic acid derivatives, whereby the reaction time before the elution of the derivatives having an intended molecular size distribution (that is, falling within the range of form 4S to 13S as the sedimentation constant value or from 50 to 10,000 or so as the number of bases) may noticeably be shortened.

In accordance with the present invention, the reaction is stopped after the detection of the completion of the sizing reaction, and then a lower alcohol is added to further process the reaction solution. Among lower alcohols, ethanol is especially preferred.

In the case of ethanol-precipitaton accoring to the present invention, for example, the yield of L-poly-C (sized poly-C) (the prefix "L- ... ") means "sized ... " hereinafter) from poly-C is 93% and the yield of L-poly-I from poly-I is 78%. Thus the yield of the sized products is high.

By contrast to this, a reaction solution is required to be put in a dialyzing tube for dialysis in the conventional manner. In this case, the recovery is only 60% or so, and the yield of L-poly-I from poly-I could be expected to be only 40% or so. In addition the dialysis operation requires 3 days or so.

However, in accordance with the ethanol-precipitation method of the present invention where ethanol is added to a reaction solution in an amount of two times of the reaction solution and stirred so as to precipitate the desired product and then the resulting precipitate is collected by centrifugation and washed and dried, the process may be completed within one hour.

The above-mentioned aspect (3) is an especially important feature of the present invention.

The reaction of substituting the nitrogen atoms in the nucleic acid moiety in a sized single-stranded nucleic acid polymer by sulfur atoms (for example, substituting the amino group in the cytidine residue moiety in poly-C by a mercapto group in a certain proportion) so as to convert the nucleic acid moiety into a different nucleic acid (the reaction being referred to as "sulfurization" herein) is often utilized in synthesis of copolymers. Another characteristic feature of the present invention is to add an aryl alcohol to the sized single-stranded nucleic acid polymers for isolation of sulfurized copolymers. This is the above-mentioned aspect (4).

As an aryl alcohol for the purpose, for example, phenol can be used.

For example, a half amount of phenol is first added to the reaction solution containing pyridine, water and hydrogen sulfide gas in mixture, stirred and centrifuged, whereby the aqueous layer is definitely separated from the phenol layer and the coloring agent in the reaction solution as well as by-produced sulphur and the like are transferred to the phenol layer. Afterwards, the aqueous layer is isolated and the intended product is precipitated by treatment with an aqueous salt solution and an alcohol. Then the thus precipitated product is isolated by centrifugation and then washed with an alcohol to obtain a purified product.

In accordance with this process, almost all the hydrogen sulfide is transferred to the supernatant in the form of a hydrogen sulfide solution and therefore this may easily be removed from the reaction product.

For example, according to the process of the present invention using phenol, the operation may be completed within one hour and the yield is almost 100%. In addition, the product may be isolated quantitatively.

The above-mentioned characteristic aspects (2) to (4) of the present invention are important for sizing prior to annealing. Namely, these are extremely essential so as to efficiently perform the process of sizing prior to annealing.

The above-mentioned aspect (5) is still another characteristic feature of the present invention, where a step of size-definition is performed between the steps of sizing and annealing. This will be explained hereunder.

In this step an ion-exchange resin is utilized. As an example of applying an ion-exchange resin to macromolecular nucleic acids, DEAE-Cellulose, DEAE-Sephadex, benzoylated DEAE-Cellulose or the like is applied to t-RNA (*BBA*, 47, 193, 1961; *BBRC*, 10, 200, 1963; *Biochem.*, 6, 3043, 1967). In the example, however, the ion-exchange resin is applied only to purification of low molecular nucleic acids having the number of bases of at most 80 or so.

The present inventors investigated various means to determine whether the intrinsic property of the charge absorbability of ion-exchange resins could be applied to purification of macromolecular nucleic acid polymers on the basis of the index of the number of bases of the polymers and, as a result, have established the present invention. Since the final products to be obtained by the present invention are extremely useful as medicines, it is believed that the size-definition to be conducted by the use of an ion-exchange resin (which will also be referred to as "ion-exchange process" herein) is an especially important feature of the method of the present invention.

In the ion-exchange process of the present invention, an ion-exchange resin may be put in a container having a nucleic acid polymer to be processed therewith so as to attain the object (batch process), but in general, column chromatography is utilized for fractionation (column process). Specifically, an ion-exchange resin is put in a column and a solution of a nucleic acid polymer is introduced into the column so that the polymer is once absorbed to the ion-exchange resin. Next, an eluent such as salt-Tris buffer or the like is linearly or step-wise passed through the column with varying the salt concentration so as to obtain a constant amount of an eluate. The number of bases of the nucleic acid polymer as contained in each fraction as eluted is detected by the same HPLC gel-filtration as above using a marker as an index, and accordingly, the fractions containing the intended final product may be collected.

In order to attain the object of the present invention by the above-mentioned ion-exchange process, the kind of the ion-exchange resin to be filled in a column as well as the kind of the eluent to be used for elution is an extremely important factor.

For example, when poly-I was dissolved in Tris-HCl buffer and was absorbed to QAE (quaternary aminoethyl) used for size-definition of poly-I, for ion-exchanging, the intended product could not be obtained even though the salt concentration in the eluent was made extremely high. This is because poly-I itself became insolubilized as the salt concentration in the eluent was higher than that of a proper eluent for poly-I on the QAE resin. This is obvious from the fact that the inosinic acid which is the constitutional unit of poly-I is structurally more hydrophobic. In this case, the salt concentration in a proper eluent for poly-I may be determined in comparison with the case of poly-C.

In another experiment conducted by the present inventors, it was observed that a solution of poly-I became white and cloudy to form a precipitate in a buffer having a proper eluent salt concentration for poly-I in a QAE resin. Accordingly, in the ion-exchange process of the present invention, it should be said that the selection of the kind of the ion-exchange resin to be used as well as the selection of the eluting salt concentration is an extremely important factor.

For example, in the case of poly-I, DEAE resin gave an extremely good result. In the case of poly-C, it was found that both QAE resin and DEAE resin could give a favorable result. For the elution, either salt linear gradient elution or salt stepwise gradient elution can be utilized, whereby the polymers can be fractionated and eluted in the order of the length of the chains of the polymers.

For instance, when poly-C (38 mg, $S_{20}$, 8.6) was absorbed to DEAE-Toyopearl 650 C ($\phi 10 \times 130$ mm) and then eluted by linear gradient elution using the following eluents (A) and (B) each in an amount of 100 ml.

(A)=0M Nacl/10 mM Tris-HCl (pH 7.0)
(B)=0.5M NaCl/10 mM Tris-HCl (pH 7.0)

The linear gradient was for (B) (from 0% to 100%); and the elution condition was as follows:

Linear flow rate: 1.32 cm/min.
Elution rate: 1.0 ml/min (175 drops/fraction).

As a result, the following fractions each having the chain length as indicated were eluted in order.

| Fraction | b.p. |
| --- | --- |
| 33 | 340 |
| 34 | 470 |
| 35 | 740 |
| 36 | 1000 |
| 37 | 1500 |

In addition, the same sample was eluted by stepwise gradient elution, whereby a fraction of lower than 500 b.p. was first eluted with 0.3M NaCl/10 mM Tris-HCl (pH 7.0) (50 ml) and then a fraction of from 500 to 1500 b.p. was eluted with 0.5M NaCl/10 mM Tris-HCl (pH 7.0) (50 ml).

In the same manner, poly-I (7.8 mg, $S_{20}$, 7.3) was eluted by linear gradient elution under the same condition as above. As a result, the following fractions were eluted in order.

| Fraction | b.p. |
| --- | --- |
| 35 | 30 |
| 36 | 140 |
| 37 | 230 |
| 38 | 350 |
| 39 | 460 |
| 40 | 540 |

In addition, the same sample was eluted by stepwise gradient elution, whereby a fraction of lower than 300 b.p. was first eluted with 0.3M NaCl/10 mM Tris-HCl (pH 7.0) (50 ml) and then a fraction of from 300 to 600 b.p. was eluted with 0.5M NaCl/10 mM Tris-HCl (pH 7.0) (50 ml).

As mentioned above, even macromolecular nucleic acids could be fractionated by the method of the present invention into chain length-defined nucleic acid fractions (size-definition) by properly selecting the salt concentration in the elution.

As illustrated in the above-mentioned two examples, fractions (main components) having a proper chain length distribution suitable for the pharmaceutical uses as medicines for humans and animals can freely be fractionated from a mixture containing various macromolecular nucleic acids with different chain length distributions, and the fractionation can be performed by an industrial mass-production scale. The characteristic in the fractionation is the most important aspect in the ion-exchange process of the present invention.

When a pharmaceutical composition is manufactured in injectable form, it is well known that an operation of removing pyrogens from the compositions is essential. The pyrogen lipopolysaccharide is known to be present and this must not be incorporated into medical compositions.

It has been found that the application of the above-mentioned ion-exchange process to the nucleic acid derivatives of the present invention is effective for removing pyrogens from the derivatives.

Accordingly, the present inventors further continued various experiments so as to more precisely investigate the above-mentioned favorable phenomenon and, as a result, it has been found that pyrogens can be removed from any and every single-stranded nucleic acid derivative irrespective of the chain length thereof by the ion-exchange process of the present invention. This is a further characteristic aspect of the present invention.

The results obtained by a limulus test of quantitatively determining the amount of endotoxin in various single-stranded RNA's (commercial poly-C and chain-shortened derivatives thereof) are shown in Table below.

In the Table, EU (endotoxin unit) means a unit in a rabbit fever test with USP reference standard endotoxin (E. coli 0113). (1) indicates a distilled water for injection (blank); (2) indicates poly-C (commercial product-1); (3) indicates poly-C (commercial product-2); and (4) indicates the product obtained in the following Example (5-4).

| Test Substance | Before or After Ion-Exchange Column | Concentration | | | |
|---|---|---|---|---|---|
| | | ug/ml | EU/ml | pg/mg | EU/mg |
| (1) | — | 29.92 | 0.0868 | | |
| (2) | Before | 308.29 | 0.8941 | 548.07 | 1.5895 |
| | After | 18.68 | 0.0542 | 33.96 | 0.0985 |
| (3) | Before | 93.89 | 0.2723 | 166.18 | 0.4819 |
| | After | 19.45 | 0.0564 | 34.12 | 0.0989 |
| (4) | Before | 89.63 | 0.2599 | 155.88 | 0.4520 |
| | After | 57.45 | 0.1666 | 114.90 | 0.3332 |

From the results of the above Table, the pyrogen-removing effect by ion-exchange is clear.

The nucleic acid derivatives of the present invention have a strong carcinostatic activity, which will be mentioned hereunder in detail. The activity is merely one of other various physiological activities of the nucleic acid derivatives of the present invention.

The nucleic acid derivatives of the present invention may be given orally, parenterally, topically or rectally. They are, of course, administered or applied in forms suitable for the particular administration or application route. For example, oral administration would be by tablets or capsules; parenteral administration by injection, infusion or inhalation; topical by lotion or ointment; and rectal by suppositories. Parenteral administration is preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintergrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginage, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear and opaque protective coating consisting of a sealing coat of shellac, a coating of sugar or polymeric material and a polish coating of wax can be provided. Dyestuffs can be added to these coatings to distinguish different unit dosages.

Oral fluids such as solutions syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

The compounds of the present invention can be used jointly with various types of biological response modifiers (BRM) described below whereby a synergistic effect in therapy and a decrease in side effects is achieved.

Examples of suitable biological response modifiers are as follows:

Interferons (alpha, beta, and gamma)
Interleukins (IL-1 and IL-2)
CSF (colony stimulating factors)
TNF (Tumor necrosis factors)
Levamisole
Bestatin
Rectinoic Acid
LAK Cells, etc.

as well as other anti-cancer drugs such as 5-FU (5-fluorouracil), Ara-C (cytosine arabinoside), Ara-A (adenine arabinoside), CDDP (cisplatin), cyclophosphamide, etc. and antiviral drugs such as azidothymidine.

The physiological activity of the Nucleic Acid Derivatives of the Present Invention thus includes:

(1.) Interferon-inducing activity

With reference to sulphurized poly C:poly I derivatives which is one of the nucleic acid derivatives of the present invention, its action as an interferon-inducer was determined by an antiviral activity assay method. The sulphurized poly C:poly I derivative used as Sample I for the test is an SH substituted derivative while Sample II is a derivative having an S—S bond. In both n has a value of 20 and residue numbers of 50 to 2,000.

The lymphocyte ($10^6$ cells per ml) obtained from human peripheral blood was treated for 2 hours with the sample (10 micrograms/ml) in a culture liquid (RPMI 1640; 20% FCS). The reacted culture liquid was removed, the cells were again floated in fresh culture liquid (RPMI 1640; 20% FCS), incubated for 20 hours, and the supernatant liquid was subjected to a usual measuring method for interferon-antiviral activity using sindbi's virus and FL cell (cf. Rinsho Kensa, 28, 1726, 1984). The result is given in the following table. The titer of interferon was measured by a dilution concentration using a CPEI50 (Cytopathogenic Effect Inhibition 50) method. Sample II is the nucleic acid derivative having an S—S bond formed from 4-thiouridine oxidation at the ratio of 20 to 1 (cytidine to 4-thiouridine) while Sample I was the SH-substituted derivative. Conventional poly I:poly C was used as a control sample.

|  | Concentrations (micrograms/ml) | | | |
| --- | --- | --- | --- | --- |
|  | 10 | 100 | 200 | 500 |
| Test Sample I | 100 | >6400 | >6400 | >6400 |
| Test Sample II | 100 | >6400 | >6400 | >6400 |
| Control Sample | 100 | 800 | 1600 | >6400 |

(Interferon titer: units/ml)

It is apparent that the nucleic acid derivative of the present invention exhibits strong action as an interferon inducer.

Among the sulphurized poly C:poly I derivatives of nucleic acid derivatives of the present invention obtained in the example given later, one with the n-value of 20 and the molecular size of 50 to 300 residue number and another with the n-value of 20 and the molecular size of 200 to 2,000 residue were used as test samples and subjected to the same physiological activity tests. Similar results were obtained. A similar result was also obtained on testing a nucleic acid derivative having an n-value of 20 and a molecular size of not less than 20,000 residue numbers before the low-molecularization.

(2.) TNF (Tumor Necrosis Factor)-inducing ability

Alveolar macrophage from rabbits pretreated with BCG at 10 to 14 days before was taken, regulated to $2 \times 10^6$ per milliliter in a 10% FCS-added RPMI 1640 medium, one milliliter of its was placed on a plastic dish, and cultured in a carbon dioxide gas incubator (5% $CO_2$) in the presence or absence of the sample at 37° C.

The supernatant liquid of cell culture after 2 or 8 hours was subjected to the TNF activity test. The result is given below. The TNF activity values were determined by measuring the cell hindrance activity to LM cell after 72 hours using the dye in-take method and the dilution (by times) at 50% cell hindrance was indicated as a titer. The fact that the cell hindrance was due to the TNF was confirmed by, using a monoclonal antibody to a rabbit TNF, its activity neutralized.

|  | TNF Activity | | Neutralization by |
| --- | --- | --- | --- |
|  | (2 hrs) | (8 hrs) | Anti-TNF Antibody |
| Control | — | — | — |
| LPS | 32 | >64 | + |
| Test Sample I | 32 | >64 | + |
| Test Sample II | 32 | >64 | + |
| Control Sample | 32 | >64 | + |

LPS was used at the concentration of 1 microgram/ml and the test and control samples were at the concentrations of 10 micrograms/ml. The test and control samples used were the same as those in (1.) It is apparent that the TNF-inducing activity of the nucleic acid derivative of the present invention is strong.

(3.) The TNF-inducing activity in vivo

Meth A tumor ($2 \times 10^5$) was transplanted behind the abdomen skin of BALB/c mice (6 to 8 weeks of age; male), drugs were given on the 2nd and 12th days after transplantation, blood was taken at one hour after the second administration, and the TNF activity in the serum was measured. The necrosis phenomenon at the cancer-carrying part occurred thereafter was also observed. The result is given below. The values in the table are the same titer as used in the above (2.)

| Treatments | | TNF Activity | |
| --- | --- | --- | --- |
| (1st) | (2nd) | in Serum | Necrosis |
| BCG | LPS | 192 | observed |
| BCG | Test Sample I | 48 | observed |
| BCG | Test Sample II | 50 | observed |
| BCG | Control Sample | 24 | observed |
| Test Sample I | Test Sample I | 12 | observed |
| Test Sample II | Test Sample II | 14 | observed |

Both test and control samples were the same as those in the above (1). It is apparent that the TNF producing ability in vivo of the nucleic acid derivative of the present invention is strong.

(4.) Inducing Activity of Interleukin 1

Mononuclear particles were separated from normal human heparin-added peripheral blood by specific gravity centrifugation method using Ficoll-Hypaque (Pharmacia, Ficollpaque, trademark), the numbers were adjusted to $5 \times 10^6$/ml in a 10% FCS-added RPMI medium, placed in a plastic dish, incubated at 37° C. for one hour, and the cohesive cells were used as an interleukin 1-producing source.

The sample to be tested was added to the $5 \times 10^5$/ml of single particle, incubated at 37° C. for 24 hours, and the interleukin 1 activity in the supernatant liquid was determined by measuring a $^3$H-thymidine in-take method into a PHA-stimulated mice thymus cells using a proliferation ability of the thymus cells as a target. The result is given in the following table. The control was physiological saline solution. The concentration of interleukin 1 was 1.25 units/ml and those of test samples I and II and of control sample were in 100α/ml.

| Samples Used | In-Take Amount (DPM ($\times 10^4$)) |
| --- | --- |
| Control | 3370 |

-continued

| Samples Used | In-Take Amount (DPM ($\times 10^4$)) |
|---|---|
| Test Sample I | 11384 |
| Test Sample II | 11560 |
| Control Sample | 8397 |
| Interleukin 1 | 12517 |

It is apparent that the nucleic acid derivatives of the present invention exhibit strong interleukin 1 inducing activity.

(5.) Inducing activity of Interleukin 2

Lymph particles obtained from spleen cells of BALB/c mice were used as a source for production of interleukin 2.

To $5 \times 10^6$/ml of Lymph particles was added the sample to be listed, the mixture was incubated at 37° C. for 24–48 hours, and the interleukin 2 activity in the supernatant liquid was determined by a $^3$H-thymidine incorporation method using CTLL-2 or NK-7 which is cell strain proliferating depending upon interleukin 2 using the proliferation ability as a target. The results are given in the followng table. The control is physiological saline solution. The interleukin 2 was in a concentration of 5 units/ml and both test I, II and control samples were in the same concentration of 100α/ml. The test and control samples used were the same as those in (1.)

| Samples | Incorporated Amount (DPM ($\times 10^3$)) |
|---|---|
| Control | 230 |
| Test Sample I | 3247 |
| Test Sample II | 3320 |
| Control Sample | 653 |
| Interleukin 2 | 3578 |

It is apparent that the nucleic acid derivatives of the present invention exhibit strong interleukin 2 inducing activity.

(6.) Macrophage Activation

Samples were administered to BALB/c mice (7–10 weeks age; male) intraperitoneally, cells exuded from the peritoneum at 3 to 5 days after administration were collected, plastic-cohesive cells (mainly macrophage) were separated as effector cells, and the macrophage activation was investigated by a $^3$H-thymidine isolation method using Meth-A tumor cell as a target (the E/T ratio being 15-20:1). The results are given in the following table. The control was 0.2 ml of physiological saline solution 50 micrograms of test sample I, II or control sample was administered. The test and control samples used were the same as those in (1.)

% Cytotoxicity was calculated by:

$$\frac{\text{(experimental value)} - \text{(background)}}{\text{(100\% .3H release)} - \text{(background)}} \times 100$$

| Samples | % Cytotoxicity |
|---|---|
| Control | 0.5 |
| Test Sample I | 10.3 |
| Test Sample II | 10.8 |
| Control Sample | 5.7 |

It is apparent that the nucleic acid derivatives of the present invention exhibit strong macrophage activation.

(7.) NK Cell Activation

The activation of NK cells in human peripheral blood was determined by measuring hindrance activity using K562 as a target cell by an isolation method of $51_{Cr}$. The result is given below. The control used was physiological saline solution. The test and control samples were the same as those in the above (1.)

| Samples (micrograms/ml) | Melting % (%$^{51}$ Cr Isolation) |
|---|---|
| Control | 30 |
| Test Samples | |
| (10) | 47 |
| (30) | 55 |
| (100) | 57 |
| (300) | 50 |
| (500) | 30 |
| Test Samples II | |
| (10) | 51 |
| (30) | 59 |
| (100) | 63 |
| (300) | 60 |
| (500) | 45 |
| Control Samples | |
| (10) | 52 |
| (30) | 60 |
| (100) | 65 |
| (300) | 62 |
| (500) | 52 |

It is apparent that the nucleic acid derivatives of the present invention exhibit NK cell activation.

(8.) Inhibitory Action for Proliferation of Tumor Cells

Inhibitory action for proliferation of cell line tumor cells was measured. Cells ($3 \times 10^4$/ml) was treated for 48 hours in a culture liquid containing 10% FCS together with samples (10 micrograms/ml and 100 micrograms/ml) and then incubated for 24 hours with tritium-labelled thymidine. The inhibition % was given by an incorporated amount of thymidine to a control which was not treated with the sample. The results are given below. The test and control samples were the same as those in above (1.)

| Cells | Inhibition % | | | | Control Samples | |
|---|---|---|---|---|---|---|
| | Test Sample I | | Test Sample II | | | micrograms/ml |
| | 100 | 10 | 100 | 10 | 100 | 10 |
| NAMALWA | 65.6 | 55.7 | 61.2 | 46.4 | 56.9 | 37.4 |
| RAJ1 | 68.3 | 58.3 | 67.8 | 61.5 | 74.7 | 69.4 |
| L929 | 36.9 | 35.7 | 36.8 | 34.7 | 32.7 | 20.5 |
| RAMOS | 52.4 | 42.2 | 45.5 | 40.5 | 52.4 | 29.9 |

It is apparent that the nucleic acid derivatives of the present invention exhibit inhibitory action for proliferation of tumor cells.

(9-i.) Inhibitory Action for Proliferation of Tumors in Cancer-Carrying Mice

The inhibitory action for tumor proliferation was measured by the following method in Meth-A cancer-carrying mice which is the transplanted same type cancer. Meth-A cell ($3 \times 10^5$/0.1 ml) was suspended in a physiological saline solution, hypodermically injected into Balb/c mice (5 weeks age; male) and, after 2 days, started in administration of the drug three times a week for two weeks. On the second day after final administration, tumor cells were extracted and the weight was measured. The results are given below. The test and control samples were the same as those in above (1.)

| Samples (micrograms/mouse) | Numbers of Mice | Mean ± S.E. | Inhibition % |
|---|---|---|---|
| Test Sample I | | | |
| (10) | 7 | 2.09 ± 0.15 | 3 |
| (30) | 7 | 1.52 ± 0.28 | 30 |
| (100) | 5 | 0.96 ± 0.43 | 56 |
| Test Sample II | | | |
| (10) | 7 | 2.10 ± 0.27 | 3 |
| (30) | 7 | 1.62 ± 0.25 | 25 |
| (100) | 7 | 0.97 ± 0.30 | 55 |
| Control Sample | | | |
| (10) | 7 | 2.12 ± 0.27 | 2 |
| (30) | 8 | 1.38 ± 0.38 | 36 |
| (100) | 8 | 1.08 ± 0.27 | 50 |

It is apparent that the nucleic acid derivatives of the present invention inhibit the proliferation of tumor cells in cancer-bearing mice.

(9-ii). Proliferation Inhibiting Action in Mice Bearing Meth-A Which is a Transplantation Cancer This action is calculated as follows: Meth-A cells ($3 \times 10^5/0.2$ ml) were dissolved in physiological saline solution, the mixture was injected subcutaneously to balb/c mice (5 weeks age; male) and, from the second day, the sample was administered for two weeks at the rate of 3 times per week. Two days after the final administration, the tumor cells were extracted and weighed. The result is given in the following table.

The test samples used were as follows:

Test samples III is poly I:poly C in which the molecular size distribution is more than 13S.

Test sample IV is poly I:poly C in which the molecular size distribution is 4S to 13S (S value = 8).

Test sample V is poly I:poly($C_{12}$,U) wherein, to 12 cytidylic acid of poly C, one uridylic acid is substituted for cytidylic acid and the molecular size distribution is 13S to 24S.

Test sample VI is poly I:poly($C_{12}$,U) in which the molecular size distribution is 4S to 13S (S value = 9).

Test sample XI is poly I:poly($C_{20}$, $S^4U$) (namely, poly C derivative in which the cytidylic acids are substituted by 4-thiouridylic acid in an amount of one 4-thiouridylic acid per 20 cytidylic acid in poly-C) having a molecular size distribution of more than 13S.

Test sample XII is poly I:poly($C_{20},S^4U$) having a molecular size distribution of from 4S to 13S (S value = 9).

The control means that only physiological saline solution was administered.

| Sample | Dose (μg/mouse) | Numbers of Mice | Inhibition % |
|---|---|---|---|
| Control Test Sample | — | 10 | — |
| III | 100 | 10 | 83* |
| IV | 100 | 10 | 63* |
| V | 100 | 10 | 73* |
| VI | 100 | 10 | 34* |
| XI | 100 | 10 | 75* |
| XII | 100 | 10 | 52* |

*: Significant difference with $p < 0.01$

It is apparent from the above result that the nucleic acid derivatives of the present invention exhibit a proliferation inhibiting effect on tumors in cancer-bearing mice.

(9-iii). The result of another test is given in the following table. The test samples used were as follows:

Test sample VII is that wherein n = 20 and the residue numbers are 50 to 10,000.

Test sample VIII is that wherein n = 20 and the residue numbers are more than 10,000.

Test sample IX is n = infinite (i.e. cytidylic acid in poly C is not substituted) and the residue numbers are 50 to 10,000.

Test sample X is that wherein n is infinite and the residue numbers are more than 10,000.

Control means that only physiological saline solution is administered.

| Samples (micrograms/mouse) | Numbers of the Mice | Mean ± S.E. | Inhibition % |
|---|---|---|---|
| Control Test Sample | 10 | 2.63 ± 0.21 | — |
| VII (100) | 10 | 1.93 ± 0.23 | 27 |
| VIII (100) | 10 | 1.57 ± 0.17 | 40 |
| IX (100) | 10 | 1.87 ± 0.29 | 29 |
| X (100) | 10 | 2.27 ± 0.18 | 25 |

It is apparent from the above result that the nucleic acid derivatives of the present invention exhibit a proliferation inhibiting effect on tumors in cancer-bearing mice.

(10) Proliferation Inhibiting Action in Nude Mice Bearing Cancer from Human Tumor Cells Each $2.5 \times 10^6$ of cell strain HeLa S3 derived from human uterus neck and cell strain Hep-2 derived from throat cancer cells were transplanted under the skin of the nude abdomen of male nude mice 5 weeks old derived from BALB/c and, on the 7th to 10th day after the transplantation, living cohesion of tumor was confirmed. Then 100 μg/mouse of test sample (intravenously) and 25 mg/kg of 5-FU (intraperitoneally) were administered twice a week for four weeks. Tumor was extracted on the fourth week after the admininstration and the weight were measured.

The results are given in the following table. The test samples used were the same as that in the above (1).

| Sample | Weight (g) ± S.E. | Inhibition Rate (%) |
|---|---|---|
| (MeLa S3) | | |
| Control | 3.85 ± 0.23 | — |
| Test Sample I | 1.57 ± 0.19 | 59 |
| Test Sample II | 1.55 ± 0.20 | 60 |
| 5-FU | 2.06 ± 0.35 | 47 |
| (Hep-2) | | |
| Control | 0.88 ± 0.07 | — |
| Test Sample I | 0.38 ± 0.07 | 57 |
| Test Sample II | 0.35 ± 0.05 | 60 |
| 5-FU | 0.56 ± 0.12 | 30 |

(11-i) Inhibitory Action Against Metastasis of Tumor Cells to Lung

To C57BL/6 Mice (male; 5 weeks age) was transplanted, to intravenous vein, $2 \times 10^5$ B16F10 cells which are transplantable melanoma of the same type and numbers of nodes moved to lung (numbers of colonies) on the second week after the transplantation was counted. The samples were administered intravenously at 24 hours prior to the transplantation of B16F10 melanoma. The numbers of cases was 9. The results are given below. The test and control samples used were the same as those in the above (1).

| Sample (micrograms/mouse) | Numbers of Nodes moved to Lung ± S.E. |
|---|---|
| Control | 112 ± 17 |
| Test Sample I | |
| (1) | 33 ± 6* |
| (10) | 21 ± 10* |
| (100) | 4 ± 2* |
| Test Sample II | |
| (1) | 21 ± 6* |
| (10) | 15 ± 4* |
| (100) | 4 ± 1* |
| Control Sample | |
| (1) | 36 ± 16* |
| (10) | 3 ± 0.7* |
| (100) | 7 ± 3* |

*: p < 0.01

(11-ii) The results in which test samples III and IV were used is as follows:

| Samples | Doses ($\mu$g/kg) | Numbers of Colonies | Inhibition % |
|---|---|---|---|
| Control | — | 85 ± 5 | |
| Test Sample III | 5 | 25 ± 8* | 71 |
| | 50 | 11 ± 3* | 87 |
| | 500 | 1 ± 1* | 99 |
| Test Sample IV | 5 | 58 ± 8* | 33 |
| | 50 | 24 ± 7* | 72 |
| | 500 | 13 + 2* | 84 |

*significant difference with p < 0.01

It is apparent that the nucleic acid derivatives of the present invention exhibit strong inhibitory action against proliferation of the tumor cells.

Safety of the Nucleic Acid Derivatives of the Present Invention

The sample was injected intravenously to BALB/c mice (8 weeks age; male; each group comprises 5 mice) at the dose of 100 micrograms/mouse and, after 24 hours, bone marrow cells of them were collected. The cells were fixed and dyed with Giemsa. Cells of the smeared sample were observed with a microscope and the degree of appearance of reticulocytes was counted by %. Known poly I:poly C was used as a control. Physiological saline solution was administered to the control. The results are given in the following table:

| | Erythrocyte Cells (%) |
|---|---|
| Control | 40 |
| Test Sample I | 38 |
| Test Sample II | 39 |
| Control Sample | 11 |

This is clear evidence that the nucleic acid derivatives of the present invention exhibit high safety.

(2) Cytotoxic effects of the nucleic acid derivatives of the present invention to bone marrow stem cells of mice was tested. The test samples III, IV, V, VI, XI and XII used were the same as those already used and, as a control, physiological saline solution was administered.

The sample was intravenously injected to BALB/c mice (8 weeks age; male; each group comprising 5 mice) at the dose of 0.5 mg/kg and, after 24 hours, the bone marrow cells of the mice were collected. The cells were fixed, subjected to a Giemsa staining, cells in the resulting smeared sample were observed with a microscope and, depending upon the numbers of appearance of reticular erythrocytes in each sample, the rate of change was calculated in accordance with the following expression.

$$\text{Rate of Change} = \frac{(\text{Control}) - (\text{Each Test Sample})}{\text{Control}} \times 100$$

| Test Sample: | III | IV | V | VI | XI | XII |
|---|---|---|---|---|---|---|
| Rate of Change: | 61 | 0 | 59 | 0 | 30 | 0 |

Again, it is quite apparent that nucleic acid derivatives of the present invention exhibit very high safety.

(3) The same test as above using Test Samples VII to X was conducted. The result is as follows:

| Test Sample: | VII | VIII | IX | X |
|---|---|---|---|---|
| Rate of Change: | 0 | 40 | 0 | 61 |

Once again, the derivatives of the present invention were found to be very safe.

The nucleic acid derivatives of the present invention were examined for pyrogenic effects.

Injection of poly I:poly C in vivo has been known to be pyrogenic. As a result of a pyrogen test to rabbits, it has been found that the poly I:poly C gives 1.45° C. of body temperature rise in average. On the contrary, the nucleic acid derivatives of the present invention (both SH and S—S substances in the above cytotoxic experiment) show only 0.25° C. rise in body temperature on average and the result of the pyrogenic test was negative. In those experiments, three rabbits per group were used and a solution of the sample (0.2 microgram/kg) in 10 ml of physiological saline solution was intravenously injected beneath the ear of the rabbits and the body temperature at 4 hours after the injection was observed.

This is further evidence that the nucleic acid derivatives of the present invention exhibit very safe.

The result of acute toxicity tests of the nucleic acid derivatives of the present invention are set forth below.

(1) With reference to normal ddY mice, the dose of the nucleic acid derivatives of the present invention is restricted by the upper limit of the solubility of the drug given and the LD50 value was not less than 394 mg/kg. The effect was judged by whether the mouse was dead or alive one week after the intravenous injection. The similar test using other mice strains (C57BL6 and BALB/c) also gave the result that the nucleic acid derivatives (the same as above) of the present invention show much lower toxicity than known poly I:poly C.

This toxicity data is further evidence of the safety of the nucleic acid derivatives of the present invention.

| Strain | Route of Administration | $LD_{50}$ | | |
|---|---|---|---|---|
| | | Test Sample I | Test Sample II | Control Sample |
| ddY | intraveneously | >394 mg/kg | >394 mg/kg | 132 mg/kg |

(2) An acute toxicity test was conducted using BALB/c mice. The sample was administered once intravenously and, out of the numbers of dead mice after one week, LD$_{50}$ was calculated. The result is as follows:

| Strains | Route of Administration | LD$_{50}$ Test Sample III | Test Sample IV |
|---|---|---|---|
| Balb/c | i.v. | 35 mg/kg | >150 mg/kg |

It is evident that the toxicity of the Test Sample IV was lower than III and that there is a very close relationship between the chain length and the toxicity.

The following non-limitative examples more particularly illustrate the present invention.

EXAMPLE 1-1

Synthesis of Sulphurized Polycytidylic Acid

Poly C (0.5 g) was dissolved in a mixed solvent of 4 ml of water and 2 ml of pyridine, the solution was placed in a 30 ml stainless steel reaction tube together with 5 ml of liquid hydrogen sulphide, and made to react at 37° C. for 6 hours. The pressure in the sealed tube during the reaction was 20 to 22 kg/cm$^2$.

After the reaction, the reaction tube was cooled to 0° C. or lower to decrease the pressure sufficiently and the reaction tube was opened. An excess of unreacted hydrogen sulphide was removed, the sulphurized poly C solution was transferred to a 50 ml round flask, and unreacted hydrogen sulphide was removed in vacuo. The resulting solution was dialyzed three times against Tris buffer (pH 7.5) containing 10 liters of 50 mM sodium chloride and the resulting transparent liquid was further lyophilized to give 0.47 g of white fibrous substance.

The ultraviolet absorption spectra of the resulting substance was measured in a neutral aqueous solution to give the result of FIG. 1. It is known that the maximum absorption wavelength of cytidylic acid is 271 nm and that the absorption wavelength of 4-thiouridylic acid in which —NH$_2$ group at 4-position of pyrimidine ring of cytidylic acid was substituted with an —SH group is shown at 330 nm. From the ratio of heights of peaks in FIG. 1, it has been confirmed that there is one 4-thiouridylic acid for each 20 cytidylic acid groups.

In the same manner, the reaction temperatures and reaction time of the stainless tube was varied and the sulphurized polycytidylic acids having the degrees of sulphurization as given in the following table were obtained. Here the degree of sulphurization is given by "n" means the numbers of cytidylic acid to one 4-thiouridylic acid.

| Reaction Temp. | Reaction Time | n |
|---|---|---|
| 45° C. | 12 hours | 1 |
| 45 | 6 | 6 ± 1 |
| 37 | 6 | 13 ± 2 |
| 37 | 4 | 26 ± 2 |
| 37 | 2.5 | 39 ± 2 |

EXAMPLE 1-2

Manufacture of Double Strand Nucleic Acid Derivatives

Poly I (0.64 g) and 0.6 g of sulphurized poly C obtained hereinabove (1-1) were dissolved, in the same moles, in a Tris buffer containing 50 mM of sodium chloride to make the concentration of 10-20 mg/ml and, in the water bath, the temperature was gradually raised from the room temperature to 68° C. The mixture was maintained at 68° C. for about 10 minutes, allowed to stand until it became room temperature, and stored at 4° C.

The resulting solution is lyophilized to give 1.2 g of a nucleic acid derivative having SH groups in white solid.

Then, to this was added about 10 times volume (by molar ratio) of 1N iodine solution (a mixture of ⅓ mole of iodine and ⅔ mole of sodium iodide). The mixture was well mixed to make it homogeneous and allowed to stand at 0° C. for 1 hour. The reaction solution was well dialyzed against water until the yellow color of iodine vanished.

The solution thus obtained was lyophilized to give 0.98 g of white solid.

The fact that the resulting solid contains a S—S linkage was confirmed as follows. Thus, 0.1 g of this solid was dissolved in 10 ml of Tris buffer (pH 7.5) containing 0.03M of sodium thiosulphate, stored at room temperature for 0 to 7.5 hours, and the ultraviolet absorption spectra at each time were observed. The result is given in FIG. 2. It is known that the S—S bond is generally reversible and the S—S bond cleaves by reduction giving an S—H group. With an elapse of time, a shoulder peak of 310 nm which is an absorption wavelength due to the S—S bond decreased while an absorption at 330 nm which is due to —SH substance (4-thiouridine) increased and, after 7.5 hours, the degree of absorption at 330 nm became identical with that of the sulphurized poly C before the oxidation. It is therefore apparent that the S—S bond was quantitatively reduced to —SH group by sodium thiosulfate.

EXAMPLE 1-3

Cross-Linking Structure and Biological Activity

Among the nucleic acid derivatives into which sulphur atoms are introduced, synthetic methods and physiological activities of the test sample I (having all-reduced type SH groups) and the test sample II (having all-oxidized type S—S groups) were described as hereinabove. The cross-linking substances of the nucleic acid derivatives described here are the compounds in which a part of sulphur atoms introduced into the same molecule exhibits a disulphide bond between or in the molecules.

For example, the cross-linking derivatives having 80% of —SH groups and 20% of S—S groups in the same molecule can form a multistrand cross linking structure in 20% of the total part. In other words, in the case of poly C with 1,000 b.p. for example, it has a cross linking structure with disulfide bond at ten parts. Any nucleic acid derivative having various cross-linking numbers may be easily prepared by a partial oxidation of the —SH substance under a mild condition or by a partial reduction of the S—S substance under a mild condition. The synthetic condition is the same as that described in the examples.

The ratio of the SH group numbers and the S—S group numbers, i.e. the degree of cross-linking, can be calculated as a ratio of the values obtained by dividing the ultraviolet absorbances at 310 nm of S—S group and 330 nm of SH group, respectively, by the molecular absorption coefficients.

An alternative is as follows. Thus, nucleic acid derivative is decomposed with a RNA-ase (e.g., ribonuclease P$_1$), the decomposed product is subjected to a high performance liquid chromatography (HPLC) of the reverse phase system, and 4-thiouridine (or 4-thiouridylic acid) and a bis substance formed by a disulphide bond thereof are separated, and their amounts are measured.

With reference to physiological activities, it was found that nucleic acid derivatives having any degree of cross-linking from 1 (totally S—S substance; e.g. test sample II) to 0 (totally SH substance; e.g. test sample I) exhibit the similar activity and safety as those of the aforementioned test samples I and II.

This fact suggests that, even if those nucleic acid derivatives may be partially oxidizable or reducible, they can exhibit the same stable physiological activity as the original ones.

EXAMPLE 1-4

Low-Molecularization

The —SH containing nucleic acid derivative (1 g) obtained in the Example 1-2 was dissolved in 120 ml of water and 30 ml of 5 m sodium chloride solution and 150 ml of formamide were added thereto. The mixture was vigorously stirred to give uniform solution. The reaction solution was heated at 80° C. for 8 hours, well dialyzed against water, and lyophilyzed to give 0.95 g of white solid.

When the S—S bond-containing nucleic acid derivative obtained above is subjected to low molecularization the same as above, the same result is obtained.

This was subjected to a high performance liquid chromatography by a gel filtration and the resulting pattern is given in FIG. 3. The condition applied was that TSK-gel G40000SW (0.65×60 cm) was used and, as an eluate, 50 mM Tris HCl buffer (pH 7.5) containing 0.5M sodium chloride was used.

Each arrow in the figure shows the elution position of each standard size marker (unit of said size marker was bp) and, out of FIG. 3, it is apparent that this has a maximum distribution at around 500 residue numbers and that it has a molecular size which distributes 150 to 10,000 residue numbers. The result well agreed with the value obtained from an electrophoresis using polyacrylamide gel or agarose gel. As already stated, the molecular size is indicated in this specification by the term "residue number" and, in FIG. 3, the "residue number" is in agreement with the "bp" as units.

When the reaction time and temperature of this low-molecularization was varied, the substances having the following molecular sizes were obtained by the same manner.

| Reaction Temp. | Reaction Time | Max. Distribution (bp) | Distribution (bp) |
|---|---|---|---|
| — | 0 hr | — | >20,000 |
| 80° C. | 24 | 30 | 10–55 |
| 80° C. | 16 | 200 | 50–300 |
| 80° C. | 8 | 500 | 150–1000 |
| 60° C. | 12 | 600 | 50–2000 |
| 60° C. | 8 | 1000 | 200–5000 |

Among the nucleic acid derivatives obtained by the above example, those with 50 to 2,000 residue numbers of molecular size distribution were taken and their fusing curves were measured.

Sample I or II (0.7 OD/ml) in 10 mM Tris buffer (pH 7.5) containing 0.1M sodium chloride was warmed, at the rising rate of 2° C./4 minutes, from 20° C. to 90° C., the ultraviolet absorbancy at each temperature was measured at the wavelength of 260 nm, and an increase of ultraviolet absorbancy by a hyperchromicity was represented by a relative ratio giving the state at 20° C. as a base. A Beckmann-DU-8B spectrophotometer was used for the measurement. The result is given in FIG. 4. Melting of the nucleic acid derivatives was gradually observed during 35° C. to 55° C. and, at around 59° C., a sudden fusion curve was obtained. At higher than 70° C., the curve nearly arrived at a plateau and this means the disappearance of high dimension structure and spiral structure formation by hydrogen bond of the nucleic acid derivatives.

The 50% melting temperatures ($Tm^s$) for the samples I and II were 59.5° C. and 59.3° C., respectively. Out of the calculation from the increasing/decreasing rate in ultraviolet absorbancy at 260 nm between 90° C. and 25° C., it has been confirmed that the hyperchromicity (color darkening effect) for the samples I and II were 43.5% and 42.4%, respectively. This indicates that the nucleic acid derivatives are very stable structures under physiological conditions.

EXAMPLE 2-1

Manufacture of Double Stranded Nucleic Acid Derivatives

The same moles of commercially available poly C (S value of 6–12) and poly I (S value of 6–12) were dissolved in Tris buffer containing 50 mM sodium chloride to make their concentrations 10 to 20 mg/ml. The solution was then warmed gradually from room temperature up to 68° C. on a water bath, kept at 68° C. for about 10 minutes, allowed to stand until room temperature, and stored at 4° C.

The resulting solution was lyophilyzed to give 1.2 g of white solid of nucleic acid derivative. The product obtained as such was identical with the Test Sample III (S value: 13–24).

In the manufacture of double stranded nucleic acid derivatives, copolymer of poly ($C_{12}$,U) was used in place of poly C followed by the same procedures so that poly I:poly C ($C_{12}$,U) (which was identical with the Test Sample V wherein S value was 13–24) was prepared.

In the manner described above except that a copolymer of poly($C_{20}$, $S^4U$) was used in place of poly C, a poly I:poly($C_{20}$,$S^4U$) (sample XI having S value of from 13 to 24) was obtained.

The above-given method is generally applicable and all nucleic acid derivatives mentioned in the list above can be produced as in the manufacture of poly I:poly C.

EXAMPLE 2-2

Lower-Molecularization

One gram of the Test Sample III obtained in the above 2-1 was dissolved in 120 ml of water and 30 ml of 5M sodium chloride solution and 150 ml of formamide was added thereto. The mixture was vigorously stirred to afford homogeneous solution. This reaction solution was heated at 80° C. for 8 hours, well dialyzed against water and lyophilized to give 0.95 g of white solid. This was identical with the Test Sample IV (S value=8).

One gram of the Test Sample V obtained in the above 2-1 was dissolved in 120 ml of water and to this was added 30 ml of 5M sodium chloride solution and 150 ml of formamide. The mixture was vigorously stirred to give a homogeneous solution. This reaction solution was heated at 60° C. for 12 hours, well dialyzed against water, and lyophilized to give 0.95 g of white solid which was identical with the Test Sample VI (S value=9).

One gram of the Test Sample XI obtained in the above step (1) was dissolved in 120 ml of water, and 30 ml of a solution of 5M NaCl and 150 ml of formamide were added thereto. The resulting mixture was vigorously stirred to give a homogeneous solution. After the reaction solution wa heated at 60° C. for 12 hours, this was dialyzed fully against water and then freeze-dried to give 0.95 g of a white solid. This is Test Sample XII (S value=9).

The elution patterns of those substances by a high performance liquid chromatography using gel filtration method are given in FIG. 5. The condition applied was that TSK-gel c-DNA-PW gel filtration carrier column resin was used and elution was conducted with 0.05M Tris hydrochloride buffer (pH 7.5) (containing 1 mM EDTA and 0.3M sodium chloride solution). The eluting rate was 0.2 ml/minute and each eluting time was given on the upper part of each elution pattern (on abscissa). Detection was carried out using ultraviolet absorption at 260 nm and the absorbancy at full scale of 0.04 OD/ml was given on the coordinate.

The value (bp) of marker given at the lower part of the abscissa are DNA base numbers. The marker used was the fragment of M 13 phage RF-DNA digested by restriction enzymes.

The elution pattern of the Test Sample III (which is (1) in the drawing) is similar to those of Test Sample V (which is (2) in the drawing) and Test Sample XI (which is (5) in the drawing) of them appeared at 34 minutes after the samples were applied. It has been found that this was a void region of the column and that most of them were with base numbers of more than 6,000.

It has been also found that the molecular sizes of the low-molecularized Test Sample IV (i.e. (4) in the drawing), VI (i.e. (3) in the drawing) and Test Sample XII (which is (6) in the drawing) were distributed within a specific range with a peak at around 150 and around 600, respectively.

When the molecular size is expressed in "base number", both "bp" and "base number" are identical in terms of units in FIG. 5.

Taking poly I:poly C as an example, the reaction temperature and reaction time for said low-molecularizing reaction was changed and some examples of the resulting substances with varied molecular sizes are given below.

| Reaction Temperature | Reaction Time | Maximum Distribution (Base Numbers) | Distribution (Base Numbers) |
|---|---|---|---|
| — | 0 hr | — | >10,000 |
| 80° C. | 24 | 30 | 10 to 55 |
| 80° C. | 16 | 100 | 50 to 800 |
| 60° C. | 8 | 1000 | 200 to 6,000 |
| 60° C. | 12 | 600 | 50 to 5,000 |

The above given low-molecularization was carried out with double stranded RNA. The same conditions are applicable to single stranded RNA.

EXAMPLE 3-1

Manufacture of Double-Stranded Nucleic Acid Derivatives

The same moles of the above-obtained sulphurized poly C (0.61 g) and poly I (0.63 g) were dissolved in Tris buffer containing 50 mM sodium chloride to make the concentration 10 to 20 mg/ml. The solution was gradually warmed, on a water bath, from ambient temperature to 68° C., kept it at 68° C. for about 10 minutes, allowed to stand until it became ambient temperature, and stored at 4° C.

The resulting solution was lyophilyzed to give 1.2 g of white solid of nucleic acid derivative containing —SH groups therein which is identical with Test Sample VIII.

In the manufacture of double stranded nucleic acid derivatives, poly C was used instead of sulphurized poly C followed by the same operation as above to give poly I:poly C (i.e. Test Sample X).

EXAMPLE 3-2

Low-Molecularization

One gram of the Test Sample VIII obtained in the above 3-1 was dissolved in 120 ml of water, then 30 ml of 5M sodium chloride solution and 150 ml of formamide were added thereto, the mixture was vigorously stirred, the resulting homogeneous reaction solution was heated at 60° C. for 10 hours, well dialyzed to water and lyophilized to give 0.95 g of white solid.

High performance liquid chromatographic elution pattern of the product by a gel filtration method is given in FIG. 6. The conditions applied were that TSK-gel G 4000 SW (0.65×60 cm) was used and, as an eluting solution, 50 mM Tris hydrochloric acid buffer (pH 7.5) containing 0.5M sodium chloride was used.

Each arrow in the drawing shows the eluting position of each standard marker (unit of the size marker is bp) and, out of FIG. 6, it is apparent that the product has a maximum distribution at around 500 residual groups and its molecular size is distributed 150 to 10,000 residue numbers. This result agrees with the values calculated from the polyacrylamide gel or agarose gel electrophoretic method. As already explained, molecular size is expressed by "residue numbers" in this specification and, in FIG. 6, the residue number is identical with bp.

Among the nucleic acid derivatives obtained in the above examples, those wherein the molecular size distribution is 50 to 10,000 residue numbers is the Test Sample VII.

Following the above described procedure, 1 g of Test Sample X was dissolved in 120 ml of water followed by the same treatments to give the Test Sample IX.

While the above explanation referred to double stranded RNAs, single stranded RNAs can be processed according to the same conditions.

EXAMPLE 4-1

Manufacture and Purification of L-Poly I (sized Poly I)

To 10 g of commercially available poly I was added 200 ml of distilled water, 250 ml of formamide and 50 ml of 5M sodium chloride solution and the mixture was heated at 80° C. for about 4 hours.

This was subjected to a gel filtration with an HPLC (eluting solution: 50 mM Tris hydrochloric acid buffer of pH 7.5, 0.3M sodium chloride and 2 mM EDTA;

flow rate: 0.5 ml/minute) using a column (7.88 mm ID×300 mm) of TSK gel G-DNA-PW and, when an eluate in which the retention time had a maximum at 21,86±0.2 minutes, the reaction was stopped.

To the reaction solution was added 2 times as much volume of ethanol, the resulting precipitate was collected by centrifugation (3,000 rpm: at 4° C.), washed with 70% ethanol, and dried in vacuo to give 10.2 g of L-poly I.

In the above procedures, all water and aqueous solutions used were sterilized. This is the same in the following examples too.

EXAMPLE 4-2

Manufacture and Purification of L-Poly C (sized poly C

To 10 g of poly C was added 200 ml of distilled water, 250 ml of formamide and 50 ml of 5M sodium chloride solution and the mixture was heated at 80° C. for about 4 hours. The same as in Example 4-1, the end point of the reaction was confirmed by an HPLC gel filtration (when the retention time was 21.33±0.2 minutes).

To the resulting solution was added twice as much volume of ethanol, the precipitate was collected by centrifugation (3,000 rpm; at 4° C.), washed with 70% ethanol and dried in vacuo to give 9.5 g of L-poly C.

EXAMPLE 4-3

Sulphurization of L-Poly C

The L-poly C (8.0 g) obtained in the above Example 4-2 was dissolved in 240 ml of water, the solution was placed in a 500 ml stainless steel bomb, a solution of 12 g of hydrogen sulphide in 120 ml of pyridine was added thereto with ice cooling, the bomb was sealed and warmed at 50° C. for about 10 hours. After cooling, 200 ml of phenol saturated with TE was added thereto, the mixture was stirred, centrifuged (3,000 rpm; at 15° C. for 5 minutes) and to the aqueous layer was added 1/10 times as much volume to 5M sodium chloride solution and 2 times as much volume of ethanol to give a precipitate. The precipitate was collected by centrifugation (3,000 rpm: at 4° C. for 10 minutes), washed with 70% ethanol and "dried in vacuo to give 8.0 g of L-poly($C_{20}$, $S^4U$) which means that, to 20 cytidylic acid in a sized poly C, one 4-thioridylic" acid was substituted with cytidylic acid. In the above expression, the term TE stands for 10 mM Tris hydrochloric acid buffer (pH 7.5)-1 mM EDTA.

EXAMPLE 4-4

Annealing

Six grams of L-poly($C_{20}$, $S^4U$) obtained in Example 4-3 and 6.44 g of poly I obtained in Example 4-1 were separately dissolved in 300 ml of 10 mM Tris hydrochloric acid buffer (pH 7.5)-50 mM sodium chloride solution. Both solutions were then mixed, heated up to 70° C. on a water bath, and kept for 10 minutes. The mixture was then allowed to cool overnight. This was treated with phenol and ethanol to afford precipitate. Water (about 200 ml) was added to the resulting precipitate to make it dissolved, and dialyzed against water at 4° C. The dialyzed liquid was concentrated to dryness to give 12.4 g of annealed product.

(5) Size-definition by Ion-exchange Process

The ion-exchange was conducted by stepwise elution or linear gradient elution. In both cases, the yield and the chain length of the products were almost the same, provided that the elution condition was properly selected. For the stepwise elution of L-poly-C and L-poly(C, $S^4U$), 0.15M NaCl/10 mM Tris-HCl (pH 7.0) and 1.0M NaCl/10 mM Tris-HCl (pH 7.0) were used continuously.

Regarding the stepwise elution of L-poly-I, Example (5-1) below describes the procedure.

For the linear gradiation elution of L-poly-I, the following (A) and (B) were used, and the elution was conducted under the gradient condition of the solution (B) of from 0 to 100%.

(A)=0M NaCl/10 mM Tris-HCl (pH 7.0)
(B)=0.5M NaCl/10 mM Tris-HCl (pH 7.0).

Regarding the linear gradiation elution of L-poly-C and L-poly(C,$S^4U$), Example (5-2) and (5-4) describe the procedure.

(5-1) Size-definition of L-poly-I 210 mg of the L-poly-I obtained in the above-mentioned step (1) was dissolved in 5 ml of 10 mM Tris-HCl buffer (pH 7.0) and absorbed to DEAE-Toyopearl$^{RTM}$ 650 C ($\phi$10 mm×130 mm). Then this was stepwise eluted at a linear flow rate of 1.30 cm/min, with eluents of 0.03M NaCl/10 mM Tris-HCl (pH 7.0) (50 ml) and 0.5M NaCl/10 mM Tris-HCl (pH 7.0) (80 ml). The fraction eluted with 0.5M NaCl was collected and the retention time thereof was measured by the same HPLC gel-filtration as in the above-mentioned step (1), which was 21.90±0.2 (min).

The intended final product L-poly-I (size-defined) having a base number of from 100 to 1000 was obtained with a high yield. The recovery yield was 91%.

(5-2) Size-definition of L-poly-C 610 mg of the L-poly-C obtained in the above-mentioned step (2) was dissolved in 10 ml of Tris-HCl buffer (pH 7.0) and absorbed to QAE-Toyopearl$^{RTM}$ 550 C ($\phi$10 mm×130 mm). Then this was eluted by linear gradient elution at a linear flow rate of 1.30 cm/min, whereupon the following (A) and (B) were used each in an amount of 100 ml and the elution was conducted under the gradient condition of the solution (B) of from 0 to 100%.

(A)=0.0M NaCl/10 mM Tris-HCl (pH 7.0)
(B)=1.0M NaCl/10 mM Tris-HCl (pH 7.0). The fraction as eluted at the main peak was collected and the retention time thereof was measured by HPLC gel-filtration, which was 21.35±0.2 min. The intended final product L-poly-C (size-defined) having a base number of from 100 to 1000 was obtained with a high yield. The recovery yield was 93%.

(5-3) Size-definition of L-poly($C_{12}$,U)

19 mg of poly($C_{12}$, U) (in which the cytidylic acids were substituted by uridylic acid in an amount of one uridylic acid for 12 cytidylic acids; this had a retention time of 18.67 min in the same HPLC as in the above step (1)) was dissolved in 5 ml of Tris-HCl buffer (pH 7.0) and absorbed to DEAE-Toyopearl$^{RTM}$ 650 C ($\phi$10 mm×130 mm). Then this was eluted by linear gradient elution at a linear flow rate 1.30 cm/min, whereupon the following (A) and (B) were used each in an amount of 100 ml and the elution was conducted under the gradient condition of the solution (B) of from 0 to 100%.

(A)=0.0M NaCl/10 mM Tris-HCl (pH 7.0)

(B)=0.5M NaCl/10 mM Tris-HCl (pH 7.0). The fraction as eluted at the main peak was collected and the retention time thereof was measured by HPLC gel-filtration, which was 18.97±0.2 min. The intended final product L-poly($C_{12}$, U) (size-defined) having a base number of from 100 to 1000 was obtained with a high yield. The recovery yield was 87%.

(5-4) Size-definition of L-poly($C_{20}$, $S^4U$)

600 mg of the L-poly($C_{20}$, $S^4U$) obtained in the abovementioned step (3) was dissolved in 10 ml of Tris-HCL buffer (pH 7.0) and absorbed to QAE-Toyopearl$^{RTM}$ 550 C ($\phi$10 mm×130 mm). Then this was eluted by linear gradient elution at a linear flow rate 1.30 cm/min, whereupon the following (A) and (B) were used each in an amount of 100 ml and the elution was conducted under the gradient condition of the solution (B) of from 0 to 100%.

(A)=0.0M NaCl/10 mM Tris-HCl (pH 7.0)
(B)=1.0M NaCl/10 mM Tris-HCl (pH 7.0).

The retention time was measured by HPLC gel-filtration in the same manner as in the above-mentioned step (5-2), which was 21.35±0.2 min.

The intended final product L-poly($C_{20}$, $S^4U$) (size-defined) having a base number of from 100 to 1000 was obtained with a high yield. The recovery yield was 90%.

(6) Annealing (6-1) L-poly-I and L-poly-C 3.0 g of the size-defined L-poly-C (obtained in the above step (5-2)) and 3.2 g of the size-defined L-poly-I (obtained in the above step (5-1)) were dissolved separately in 150 ml of 10 mM Tris-HCl buffer (pH 7.5)/50 mM NaCl and they were blended. The resulting solution was heated up to 70° C. in a water bath and was kept at the said temperature for 10 minutes. Afterwards, this was left to be cooled overnight as it was. After phenol-treatment and ethanol-precipitation, water (about 400 ml) was added to the precipitate formed so as to dissolve it. Then the resulting solution was dialyzed against water at 4° C. The dialysate was concentrated to dryness to obtain 6.2 g of an annealed compound.

(6-2) L-poly-I and L-poly-($C_{20}$, $S^4U$)

1.46 g of the size-defined L-poly($C_{20}$, $S^4U$) (obtained in the above step (5-4)) and 1.57 g of the size-defined L-poly-I (obtained in the above step (5-1)) were processed in the same manner as in the above-mentioned step (6-1), and 3.0 g of an annealed compound was obtained in each case.

While the invention has been described in detail and with reference to specific embodiments thereof, it will be apparent to one skilled in the art that various changes and modifications can be made therein without departing from the spirit and scope thereof.

Figure 1:
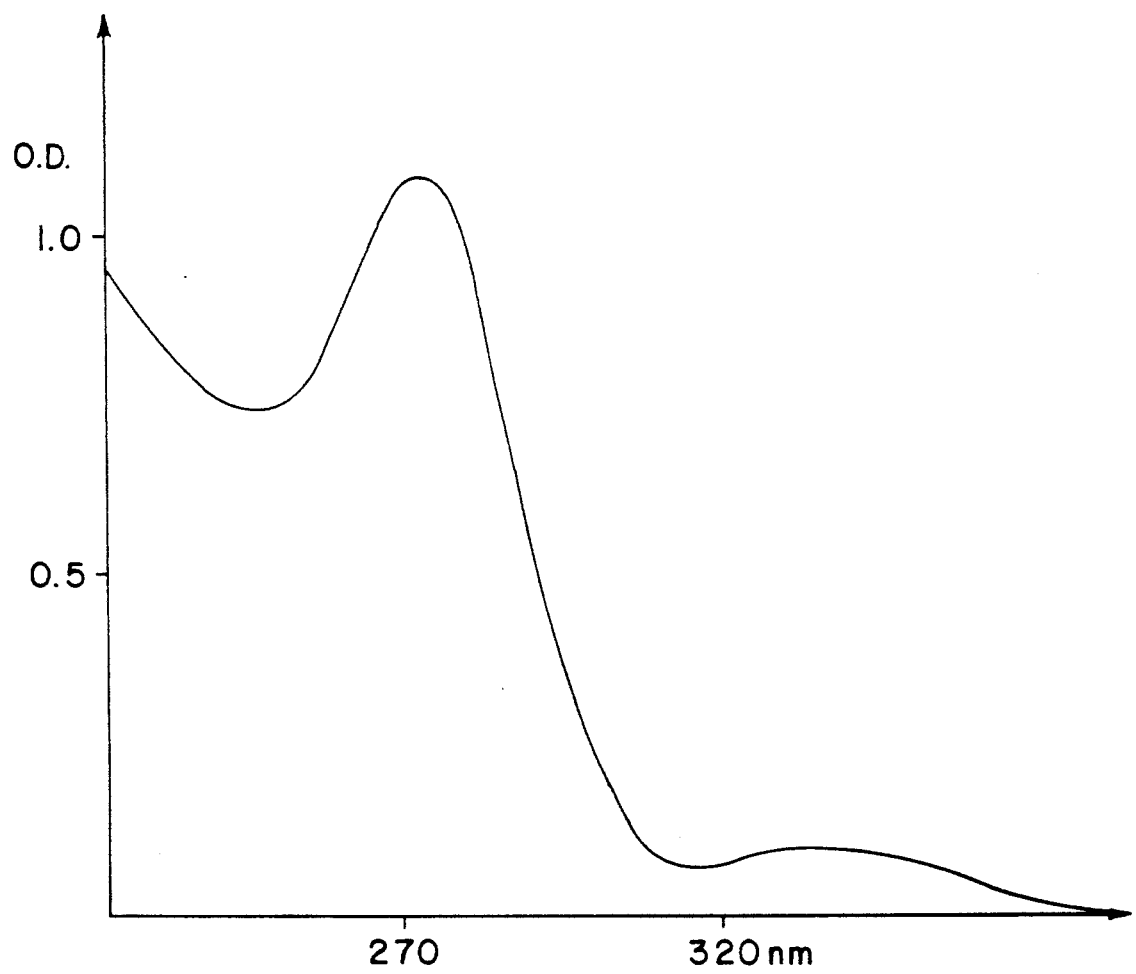
FIG. 1 shows ultraviolet absorption spectra of sulphurized polycytidylic acid obtained in Example 1. The ordinate and abscissa are absorption and wavelength (nm), respectively.
Figure 2:
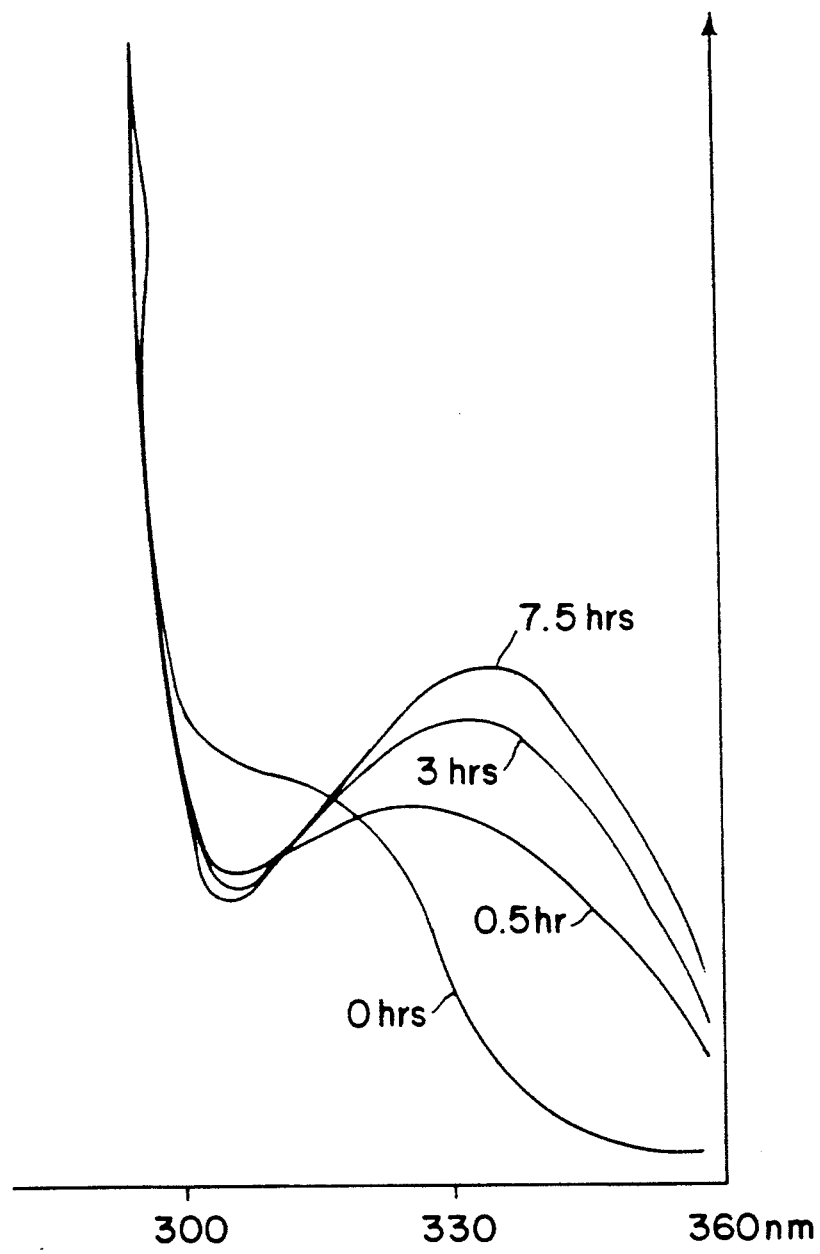
FIG. 2 shows ultraviolet absorption spectra of nucleic acid derivative obtained from Example 2. This is a UV pattern of reduction by sodium thiosulphate. The ordinate and abscissa are absorbancy and wavelength (nm), respectively.
Figure 3:
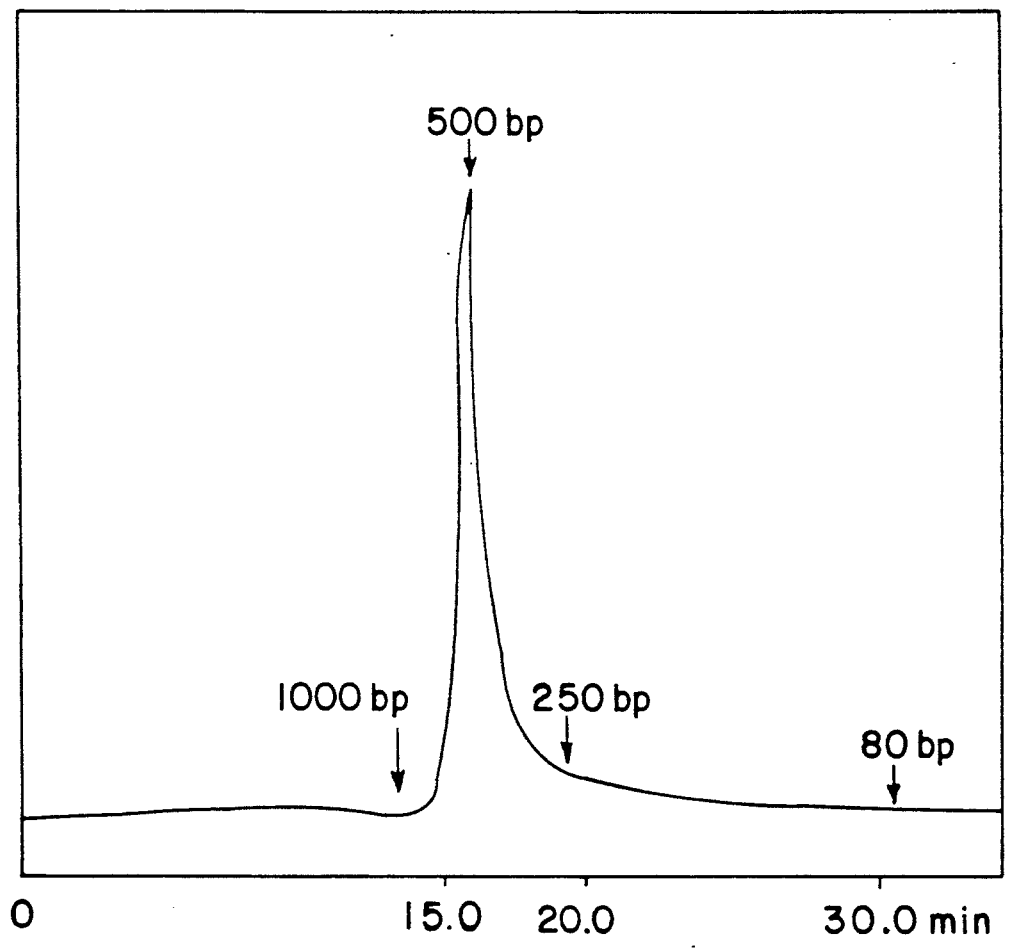
FIG. 3 shows elution patterns by high performance liquid chromatography of nucleic acid derivative of the present invention obtained from Examples 1 to 4. The abscissa and ordinate are elution time (minute) eluted amount, respectively. Each arrow indicates the eluting position of size marker.
Figure 4:
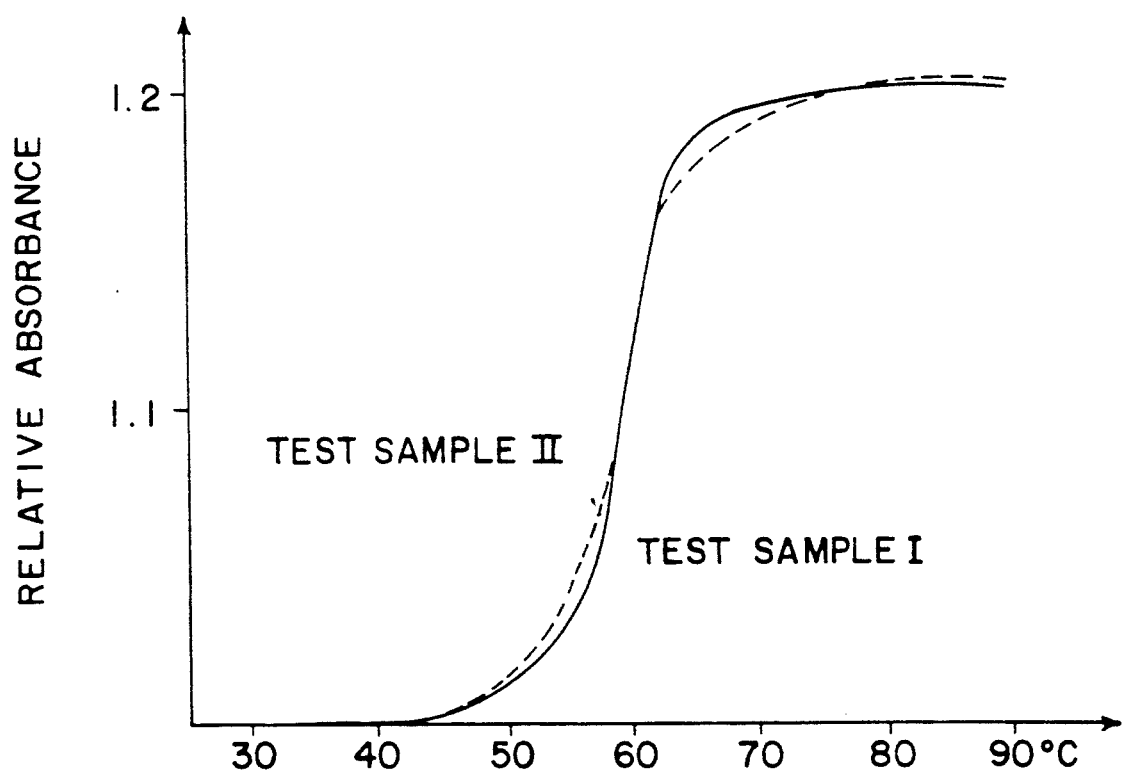
FIG. 4 shows the melting curve of the nucleic acid derivatives of the present invention in which the molecular size distribution is 50 to 2,000 residue numbers. The abscissa and ordinate are temperature (°C.) and relative absorption, respectively.
Figure 5:
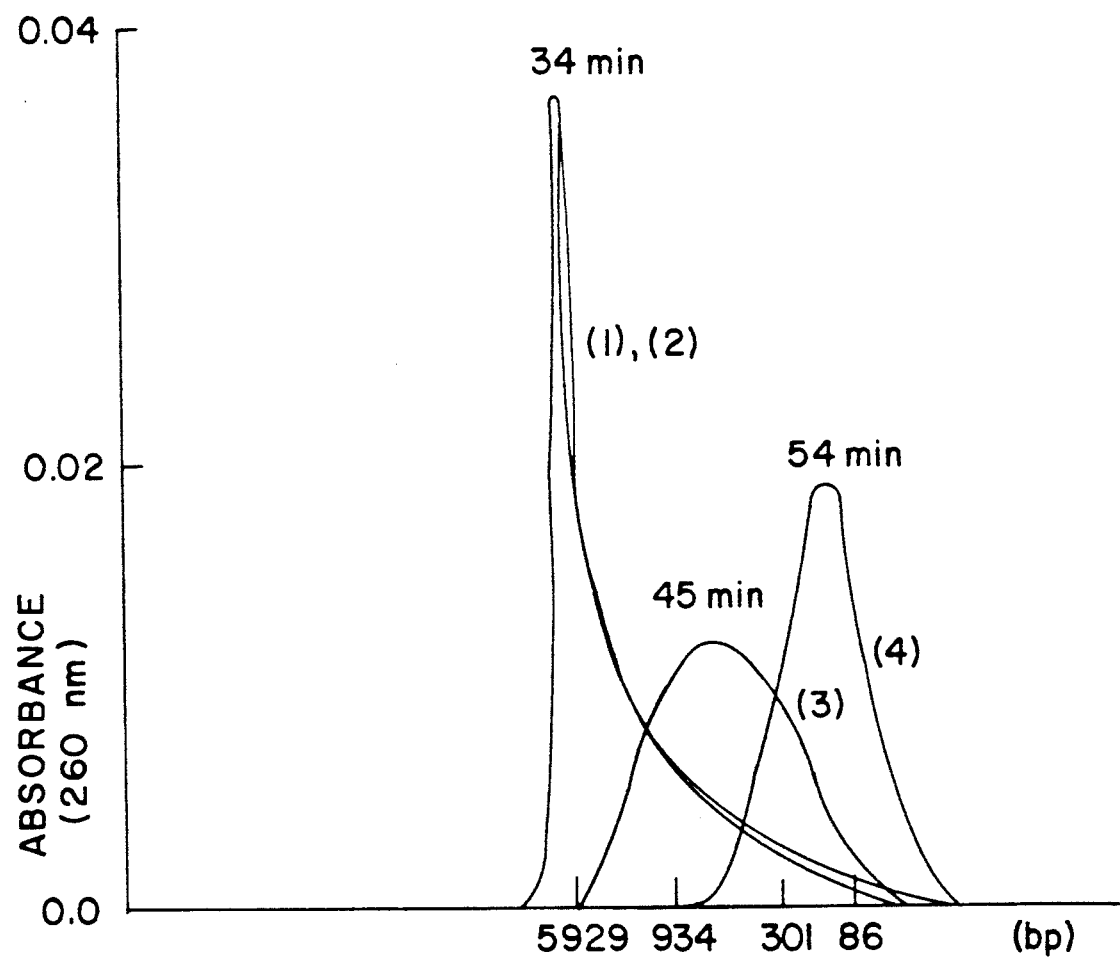
FIG. 5 shows the gel filtration elution patterns of HPLC nucleic acid derivatives of the present invention. Ordinate means absorptions at 260 nm while abscissa means retention time (in minutes) and bp corresponding thereto. (1), (2), (3), (4), (5) and (6) are Test Samples III, V, VI, XI and XII, respectively.
Figure 6:
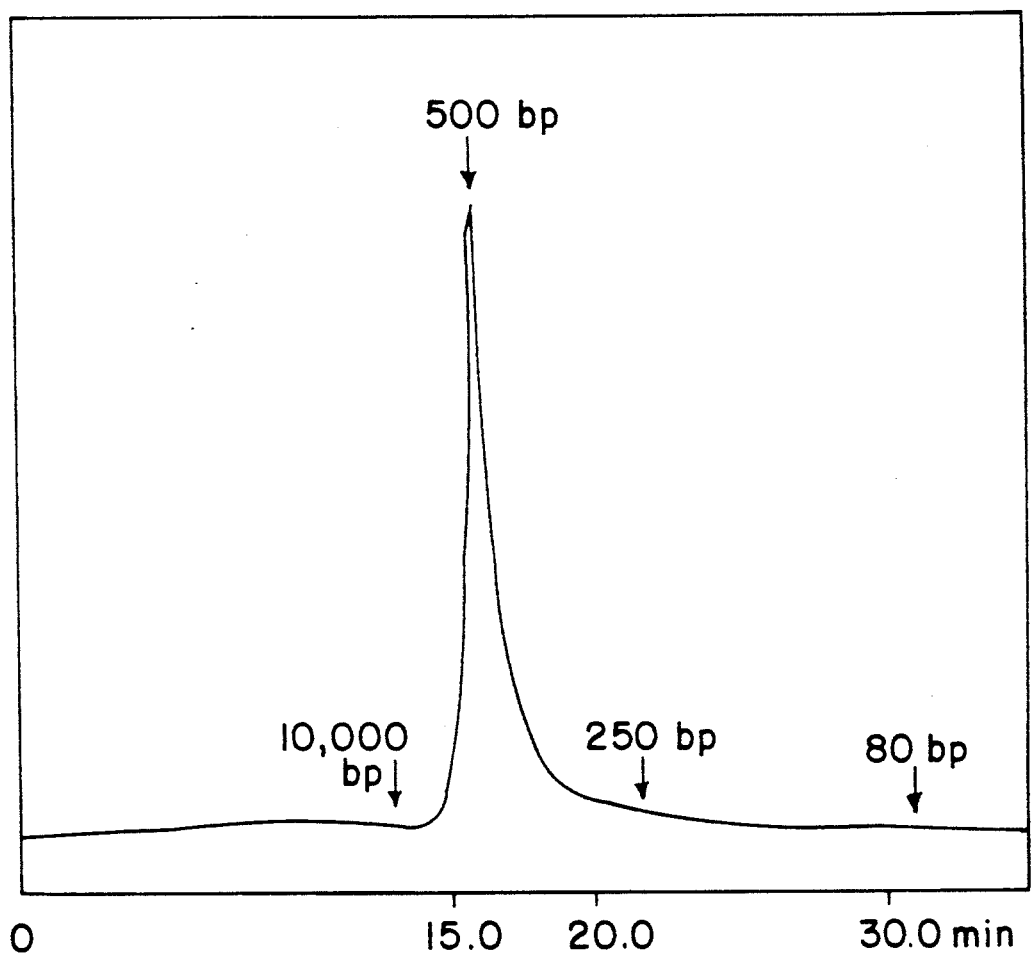
FIG. 6 shows the gel filtration patterns by HPLC of the Test Sample VII (the present invention nucleic acid derivative obtained in Example 3-2). The coordinate shows the absorption and abscissa shows eluting time as well as molecular numbers calculated from the eluting time with DNA molecular size marker. Each arrow shows the elution position of the size marker.
Figure 7:
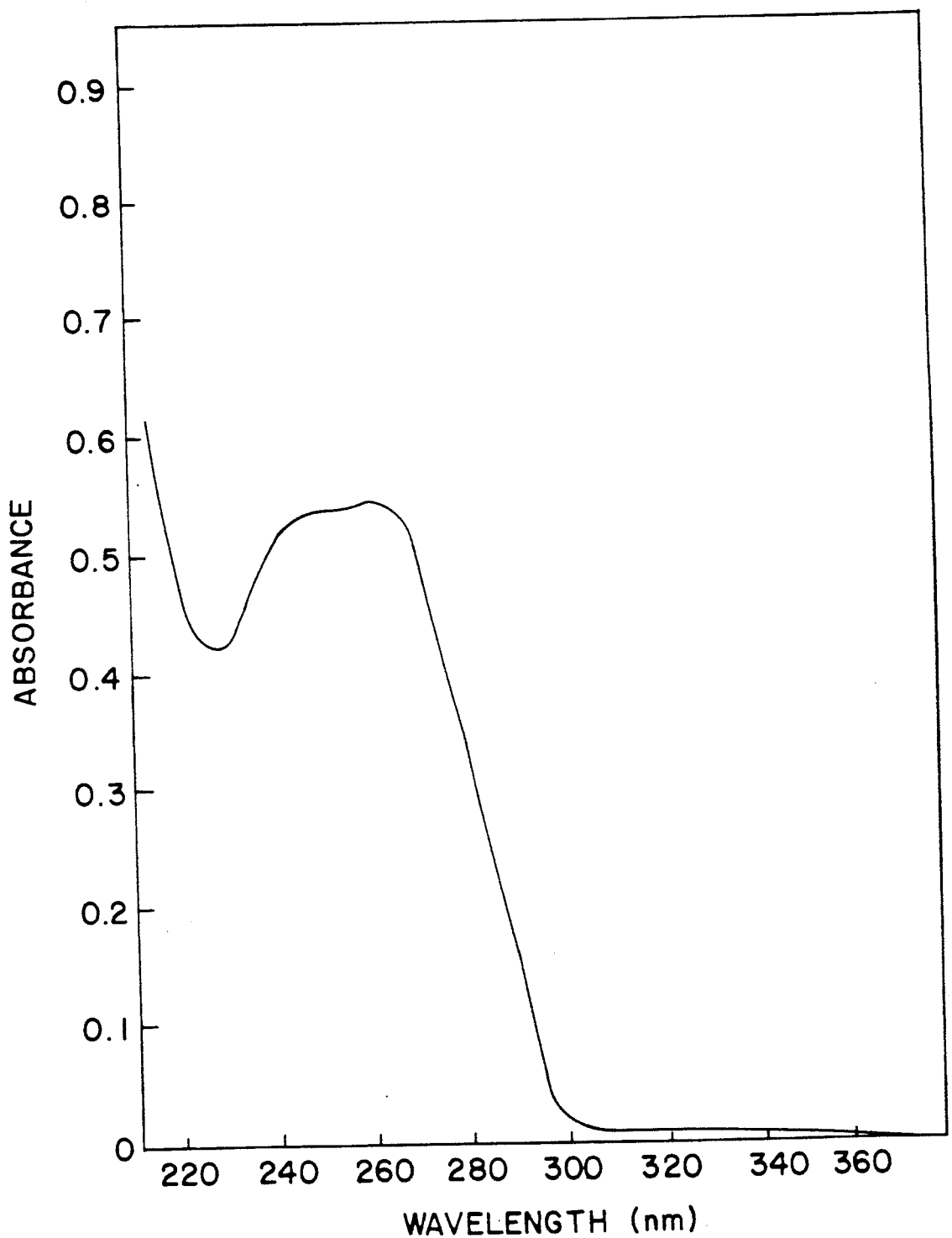
FIG. 7 shows the ultra violet absorption spectrum of the Test Sample VII. The weak absorption band at the long wavelength region (300 to 360 nm) is due to 4-thiouridine base contained in the test sample which is a nucleic acid polymer complex.

What is claimed is:

1. A double stranded RNA, wherein one of the single stranded RNAs is poly I and the other strand is poly C wherein a part of the —$NH_2$ groups on the pyrimidine ring of cytidylic acid is substituted with —SH, and further, wherein the molecular size distribution of the RNA is within the range of from 50 to 10,000 as calculated as number of bases.

2. The RNA according to claim 1 in which the maximum distribution of the molecules is at a point within the range of from 100 to 600 calculated as number of bases.

3. The RNA according to claim 1 wherein one of the —$NH_2$ groups on the pyrimidine ring of cytidylic acid is substituted with —SH for every 6 to 39 cytidylic acids in the poly C.

* * * * *